United States Patent
Grubb et al.

(10) Patent No.: US 6,498,154 B1
(45) Date of Patent: Dec. 24, 2002

(54) CYCLIC REGIMENS USING QUINAZOLINONE AND BENZOXAZINE DERIVATIVES

(75) Inventors: Gary S. Grubb, Newtown Square, PA (US); Lin Zhi, San Diego, CA (US); Todd K. Jones, Solana Beach, CA (US); Puwen Zhang, Audubon, PA (US); James P. Edwards, San Diego, CA (US); Andrew Fensome, Wayne, PA (US); Eugene A. Terefenko, Quakertown, PA (US); Jay E. Wrobel, Lawrenceville, NJ (US); Christopher M. Tegley, Thousand Oaks, CA (US)

(73) Assignees: Wyeth, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/552,357

(22) Filed: Apr. 19, 2000

Related U.S. Application Data

(60) Provisional application No. 60/183,042, filed on May 4, 1999.

(51) Int. Cl.[7] .............. A61K 31/56; A61K 31/535; A61K 31/505; A61K 31/47
(52) U.S. Cl. ................ 514/171; 514/170; 514/230.5; 514/259; 514/314
(58) Field of Search .............. 514/171, 230.5, 514/314, 259, 170

(56) References Cited

U.S. PATENT DOCUMENTS

| | | | |
|---|---|---|---|
| 3,635,964 A | 1/1972 | Skorcz et al. ............ 260/247.1 |
| 3,917,592 A | 11/1975 | Kobzina ................. 260/244 |
| 4,093,730 A | 6/1978 | Butti .................... 424/270 |
| 4,258,185 A | 3/1981 | Nakao et al. |
| 4,440,785 A | 4/1984 | Walsh ................... 424/317 |
| 4,581,356 A | 4/1986 | Teraji et al. |
| 4,666,913 A | 5/1987 | Kubla et al. ............. 514/259 |
| 4,670,566 A | 6/1987 | Walsh ................... 548/485 |
| 4,721,721 A | 1/1988 | Kuhla ................... 514/312 |
| 4,818,755 A | 4/1989 | Kuhla et al. |
| 4,822,794 A | 4/1989 | Spada ................... 514/230 |
| 4,831,027 A | 5/1989 | Narr et al. .............. 514/212 |
| 4,840,955 A | 6/1989 | Sircar |
| 4,853,473 A | 8/1989 | Fischer et al. ........... 549/326 |
| 4,868,300 A | 9/1989 | Kuhla et al. |
| 4,916,128 A | 4/1990 | Jonas et al. |
| 5,007,952 A | 4/1991 | Kume et al. .............. 71/73 |
| 5,171,851 A | 12/1992 | Kim et al. ............... 544/50 |
| 5,358,949 A | 10/1994 | Tabusa et al. |
| 5,414,088 A | 5/1995 | Von Der Saal et al. ..... 546/158 |
| 5,453,516 A | 9/1995 | Fischer et al. ........... 548/543 |
| 5,475,020 A | 12/1995 | Johnson et al. ........... 548/466 |
| 5,521,166 A | 5/1996 | Grubb ................... 514/170 |
| 5,681,817 A | 10/1997 | Hodgen et al. ............ 514/12 |
| 5,688,808 A | 11/1997 | Jones et al. ............. 514/285 |
| 5,688,810 A | 11/1997 | Jones et al. ............. 514/311 |

(List continued on next page.)

FOREIGN PATENT DOCUMENTS

| | | |
|---|---|---|
| DE | 3633861 | 4/1988 |
| DE | 43 30 234 | 3/1995 |
| DE | 43 44 463 | 6/1995 |
| EP | 022317 | 1/1981 |
| EP | 0 208 510 | 1/1987 |
| EP | 311135 | 4/1989 |
| EP | 385850 | 9/1990 |

(List continued on next page.)

OTHER PUBLICATIONS

R.M. Evans, "The Steroid and Thyroid Hormone Receptor Superfamily", *Science*, 240:889 (May 13, 1988).

A. Ulmann et al., "Clinical Uses of Mifepristone (MFP)", *Ann. N.Y. Acad. Sci.*, 261:248 (Jun. 12, 1995).

R. Kekkonen et al., "Sequential Regiment of the Antiprogesterone RU486 and Synthetic Progestin for Contraception", *Fertility and Sterility*, 60(4):610 (Oct. 1993).

(List continued on next page.)

*Primary Examiner*—Russell Travers
*Assistant Examiner*—San-ming Hui
(74) *Attorney, Agent, or Firm*—Howson and Howson

(57) ABSTRACT

This invention relates to cyclic combination therapies utilizing, in combination with progestins, estrogens, or both, compounds which are progesterone receptor antagonists of the general structure:

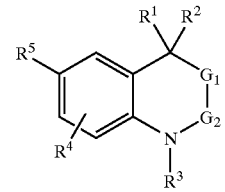

wherein: $R^1$ and $R^2$ are H, $COR^A$, or $NR^BCOR^A$, alkyl, alkenyl, alkynyl, cycloalkyl, aryl, or heterocyclic; or $R^1$ and $R^2$ fuse to form 3 to 8 membered spirocyclic alkyl, alkenyl or heterocyclic rings; $R^A$ is H or optionally substituted alkyl, aryl, alkoxy, or aminoalkyl groups; $R^B$ is H or alkyl; $R^3$ is H, OH, $NH_2$, $COR^C$ or alkyl, alkenyl, or alkynyl; $R^C$ is H, alkyl, aryl, alkoxy, or aminoalkyl; $R^4$ is H, halogen, CN, $NO_2$, alkyl, alkynyl, alkoxy, amino or aminoalkyl; $R^5$ is benzene or 5- or 6-membered heterocyclic ring; $R^6$ is H or alkyl; $G_1$ is O, $NR_7$, or $CR_7R_8$; $G_2$ is CO or $CR_7R_8$; provided that when $G_1$ is O, $G_2$ is $CR_7R_8$, and $G_1$ and $G_2$ cannot both be $CR_7R_8$; $R_7$ and $R_8$ are H or an optionally substituted alkyl, aryl, or heterocyclic moiety; or pharmaceutically acceptable salt thereof. These methods may be used for contraception or treatment and/or prevention of secondary amenorrhea, dysfunctional bleeding, uterine leiomyomata, endometriosis; polycystic ovary syndrome, carcinomas and adenocarcinomas of the endometrium, ovary, breast, colon, prostate, or minimization of side effects or cyclic menstrual bleeding. Additional uses of the invention include stimulation of food intake.

17 Claims, No Drawings

U.S. PATENT DOCUMENTS

| | | | |
|---|---|---|---|
| 5,693,646 A | 12/1997 | Jones et al. | 514/285 |
| 5,693,647 A | 12/1997 | Jones et al. | 514/285 |
| 5,696,127 A | 12/1997 | Jones et al. | 514/285 |
| 5,696,130 A | 12/1997 | Jones et al. | 514/291 |
| 5,696,133 A | 12/1997 | Pooley et al. | 514/314 |
| 5,719,136 A | 2/1998 | Chwalisz et al. | 514/170 |
| 5,733,902 A | 3/1998 | Schneider | 514/177 |
| 5,808,139 A | 9/1998 | Pathirana | 560/138 |
| 5,874,430 A | 2/1999 | Christ | 514/229.8 |
| 6,077,840 A | 6/2000 | Kurihara | 514/232.8 |

FOREIGN PATENT DOCUMENTS

| | | |
|---|---|---|
| EP | 483077 | 9/1991 |
| EP | 454330 | 10/1991 |
| EP | 0 535 529 | 9/1992 |
| EP | 510235 | 10/1992 |
| EP | 947 507 | 10/1999 |
| EP | 978 279 | 2/2000 |
| JP | 63112584 | 5/1988 |
| WO | WO 86/03749 | 7/1986 |
| WO | WO 91/04974 | 4/1991 |
| WO | WO 91/06545 | 5/1991 |
| WO | WO 93/12085 | 6/1993 |
| WO | WO 94/14434 | 7/1994 |
| WO | WO 94/29272 | 12/1994 |
| WO | WO 95/11013 | 4/1995 |
| WO | WO 95/20389 | 8/1995 |
| WO | WO 95/20972 | 8/1995 |
| WO | WO 95/33746 | 12/1995 |
| WO | WO 96/15794 | 5/1996 |
| WO | WO 96/19458 | 6/1996 |
| WO | WO 96/19997 | 7/1996 |
| WO | WO 97/13767 | 4/1997 |
| WO | WO 97/49407 | 12/1997 |
| WO | WO98/10765 * | 3/1998 |
| WO | WO 98/14436 | 4/1998 |
| WO | WO 98/27059 | 6/1998 |
| WO | WO 98/55116 | 12/1998 |
| WO | WO 99/10325 | 3/1999 |
| WO | WO 99/11264 | 3/1999 |
| WO | WO 99/15500 | 4/1999 |
| WO | WO 99/15524 A | 4/1999 |
| WO | WO 99/44608 | 9/1999 |

OTHER PUBLICATIONS

K. Horwitz et al., "Progestin, Progesterone Receptors, and Breast Cancer", "Horm. Cancer", publisher: Birkhaeuser, Boston, Mass., ed. Vedeckis, p. 283–306 (1996) abstract only.

A. A. Murphy et al., "Regression of Uterine Leiomyomata in Response to the Antiprogesterone RU 486", *J. Clin. Endo. Metab.*, 76(2):513 (Feb. 1993).

L. M. Kettel et al., "Endocrine Response to Long–Term Administration of the Antiprogesterone RU486 in Patients with Pelvic Endometriosis", *Fertility and Sterility*, 56(3):402 (Sep. 1991).

H. Michna et al.,"Differentiation Therapy with Progesterone Antagonists", *Ann. N.Y. Acad. Sci.*, 761:224 (Jun. 1995).

L. Zhi et al., "5–Aryl–1,2–Dihydrochromeno[3,4–f]quinolines: A Novel Class on Nonsteroidal Human Progesterone Receptor Agonists", *J. Med. Chem.*, 41(3):291 (Oct. 22, 1998).

D. W. Combs et al., "Nonsteroidal Progesterone Receptor Ligands. 2. High–Affinity Ligands with Selectivity for Bone Cell Progesterone Receptors",*J. Med. Chem.*, 38:4880 (Dec. 8, 1995).

K. L. Perlman et al., "20–Oxopregnacalciferols: Vitamin D Compounds that Bind the Progesterone Receptor", *Tet. Letters*, 35(15):2295 (1994).

L. G. Hamann et al., "Synthesis and Biological Activity of Novel Nonsteroidal Progesterone Receptor Antagonists", *Ann. N.Y. Acad. Sci.*, 761:383 (Jun. 12, 1995).

R. H. K. Chen et al., "Synthesis and SAR of a Novel Series of Spirobenzothlzaepine Derivatives with Antiprogestin Activity", POI–37, $16^{th}$ Int. Cong. Het. Chem., Montana (1997).

B. Narr et al., "Preparation, Testing, and Formulation of Imidazobenzoxazinones as Cardiotonics", *Chemical Abstracts*, 109:22973 (1988).

R. J. Hartmann et al., "Effects of Brofoxine, A New Anxiolytic on Experimentally Induced Conflict in Rats", *Proc West. Pharmacol. Soc.*, 21:51–55 (1978).

B. Singh et al., "Novel cAMP PDE III Inhibitor: Imidazo [4,5–b]pyridin–2(3H)–ones and Thiazolo[4,5–b] pyridin–2(3H)–ones and Their Analogs", *J. Med. Chem.*, 37:248 (Jan. 21, 1994).

A. Andreani et al., "Potential Antitumor Agents XVII ( 1). Cytotoxic Agents from Indole Derivatives and Their Intermediates", *Acta. Pharm. Nord.*, 2(6):407 (1990).

Sakata et al., "Silver Halide Photographic Materials Useful for Platemaking", *Chemical Abstracts*, 123:301431 (1993).

P. Pflegel et al., "Polarografie con 7–Chlor–5–phenyl–2–thioxo–1H–2,3–dihydro–1,3,4–benzotriazepinen", *Pharmazie*, 37(10): 714–717 (1982).

E. I. Barengolts et al., "Progesterone Antagonist RU 486 Has Bone–Sparing Effects in Ovarioectomized Rats", *Bone*, 17(1):21 (Jul. 1995).

E. V. Gromachevskaya et al., "Studies of 4H–3, 1–Benzoxazines", *Chem. Heterocycl. Cmpds.* 33(10):1209–1214 (1997).

D. Chiarino et al., "2, 1– Benzisothiazoline 2, 2–Dioxide and Derivatives", *J. Heterocycl. Chem.*, 23(6):1645–1649 (Nov.–Dec. 1986).

A. Turck et al., "On the Metabolism of 3–Substituted and 3,6–Disubstituted Pyridazines", *Tetrahedron*, 49(3):599–606 (1993).

V. Kumar et al., "Synthesis of 7–Azaindole and 7–Azaoxindole Derivatives through a Palladium–Catalyzed Cross–Coupling Reaction", *J. Org. Chem.*, 57(25):6995–6998 (1992).

P. Canonne et al., "Spirocyclization of 1–(o–Aminophenyl) cycloalkanols and 1–(2'–Amino–3'–pyridinyl)cycloalkanols", *J. Heterocyclic Chem.*, 26:113 (Jan.–Feb. 1989).

M–C. Forest et al., "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", *J. Med. Chem.*, 35:163–172 (Jan. 1992).

D. W. Combs et al., "Heteroatom Analogues of Bemoradan: Chemistry and Cardiotonic Activity of 1, 4–Benzothiazinylpyridazinones",*J. Med. Chem.*, 35:172–176 (Jan. 1992).

Kurihari et al., "Synthesis of (±)–PF1092A, B, and C; New Nonsteroidal Progesterone Receptor Ligands", *J. Antibiotics*, 50(4):360 (Apr. 1997).

A. Kende et al., "Regioselective C–3 Alkylation of Oxindole Dianion", *Synth. Commun. 12*(1):1 (1982).

T. Tucker et al., "Synthesis of a Series of 4–(Arylethylnyl)–6–Chloro–4–Cyclopropyl–3, 4–dihydroquinazolin–2(1H)–ones as Novel Non–Nucleoside HIV–1 Reverse Transcriptase Inhibitors", *J. Med. Chem.*, 37:2347–2444 (Jul. 22, 1994).

J. P. Edwards et al., "5–Aryl–1,2–Dihydro–5H–Chromeno [3,4–f]Quinolines as Potent, Orally Active, Nonsteroidal Progesterone Receptor Agonists: The Effect of D–Ring Substituents", *J. Med. Chem.*, 41:303–310 (Jan. 29, 1998).

Derwent WPI abstract, "New Imidazo–Pyridine Derivatives—Useful us Platelet Agglutination Inhibitor, Antiallergic, Antiinflammatory Sedative, Cardiac, and Cardiovascular Vasodilators", JP 63112584.

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850.

Derwent WPI abstract, F. Arndt et al., "New Heterocycle substituted Benzo–Fused Azine and Azole Derivatives—Useful as Selective Herbicides for Pre or Post–Emergence Application", EP 311135.

K. Horwitz et al., "Progestin, Progesterone Receptors, and Breast Cancer", "Hormones and Cancer", publisher: Birkhaeuser, Boston, Mass., ed. Vedeckis, p. 283–306 (1996).

Mamaev, V.P., et al., "Synthesis of 4H–Thieno [3,2–B] Pyrrol–5(6H)–One" Bulletin of the Academy of Sciences on the USSR: Division of Chemical Science, US, Consultants Bureau. New York. vol. 9, p. 1549–1553, 1966.

Derwent WPI Abstract, Chwalisz, K., et al. "Female Contraceptive Method Comprises Gestation Treatment with Intermittent Progesterone Antagonist Administration.", DE 4,330,234 (Mar. 1995).

Derwent WPI Abstract, Chwalisz, K., et al. "Contraceptive Pack for Implantation Inhibition—Contains Competitive Progesterone Antagonist and Gestagen for Sequential Oral Administration.", DE 4,344,463 (Jun. 1995).

Kolasa, K., et al., "Preliminary Pharmacological Studies of the Central Action of Phenyl and Piperidinomethyl Derivatives of 2–Benzoxazolone." *Chemical Abstracts*, vol. 99, No. 1, Abst. No. 157a, Jul. 4, 1983.

Meanwell N.A., et al., "Regiospecific Functionalization of 1,3–dihydro–2H–Benzimidazol–2–One and Structurally Related Cyclic Urea Derivatives" *J. Organic Chem.*, 60(6): 1565–82 (Mar. 24, 1995).

Singh, B., et al., "An Efficient and Novel Synthesis of Fused Thiazol–2(3H)–ones" *Heterocycles*, 36(1): 133–134, p. 136, compounds 16a, 18a, Jan. 1993.

Vernin, G.,et al., "Etude Dans la Serie des Radicaux Heterocycliques. Partie XV. Decomposition aprotique de 1' amino–6–ethyl–2–benzothiazole dans des substrats aromatiques et heteroaromatiques: preparation des mesityl–6– et furyl–6–ethyl–2–benzothiazoles, des sels quaternaires et des spiropyrannes correspondants" *Helvetica Chimica Acta*, 62(1/3):21–30 Jan. 24, 1979.

Hirota et al., "Novel Synthesis of Pyrido [3,4–d] Pyrimidines, Pyrido [2,3–d] Pyrimidines, and Quinazolines via Palladium–Catalyzed Oxidative Coupling", *Heterocycles*, 37(1): 563 (1994).

Kono et al., "New 1,2,3,4–tetrahydroquinoline–carboxylic acid derivatives—useful for treating bone metabolism disorders, e.g., osteoporosis", English Abstract of Japanese Patent No. 4–316557.

Takatani et al., "Dialkyl–oxo benzoxazolinyl inidazolinone derivatives—useful for cardiac treatment", English Abstract of Japanese Patent No. 61–191681.

* cited by examiner

CYCLIC REGIMENS USING QUINAZOLINONE AND BENZOXAZINE DERIVATIVES

This application claims the benefit of the priority of U.S. Provisional Patent Application No. 60/183,042, filed May 4, 1999.

FIELD OF THE INVENTION

This invention relates to regimens of administering compounds which are antagonists of the progesterone receptor in combination with a progestin, an estrogen, or both.

BACKGROUND OF THE INVENTION

Intracellular receptors (IR) form a class of structurally related gene regulators known as "ligand dependent transcription factors" (R. M. Evans, Science, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist. PR agonists (natural and synthetic) are known to play an important role in the health of women. PR agonists are used in birth control formulations, typically in the presence of an ER agonist. ER agonists are used to treat the symptoms of menopause, but have been associated with a proliferative effect on the uterus that can lead to an increased risk of uterine cancers. Co-administration of a PR agonist reduces or ablates that risk.

PR antagonists may also be used in contraception. In this context they may be administered alone (Ulmann, et al, Ann. N.Y Acad. Sci., 261, 248, 1995), in combination with a PR agonist (Kekkonen, et al, Fertility and Sterility, 60, 610, 1993) or in combination with a partial ER antagonist such as tamoxifen (WO 96/19997 A1 Jul. 4, 1996). PR antagonists may also be useful for the treatment of hormone dependent breast cancers (Horwitz, et al, Horm. Cancer, 283, pub: Birkhaeuser, Boston, Mass., ed. Vedeckis) as well as uterine and ovarian cancers. PR antagonists may also be useful for the treatment of non-malignant chronic conditions such as fibroids (Murphy, et al, J. Clin. Endo. Metab., 76, 513, 1993) and endometriosis (Kettel, et al, Fertility and Sterility, 56, 402, 1991). PR antagonists may also be useful in hormone replacement therapy for post menopausal patients in combination with a partial ER antagonist such as tamoxifen (U.S. Pat. No. 5,719,136). PR antagonists, such as mifepristone and onapristone, have been shown to be effective in a model of hormone dependent prostate cancer, which may indicate their utility in the treatment of this condition in men (Michna, et al, Ann. N.Y. Acad. Sci., 761, 224, 1995).

Jones, et al, (U.S. Pat. No. 5,688,810) describe the PR antagonist dihydroquinoline 1.

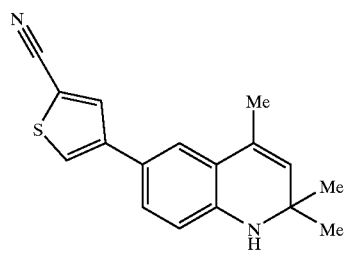

Jones, et al, described the enol ether 2 (U.S. Pat. No. 5,693,646) as a PR ligand.

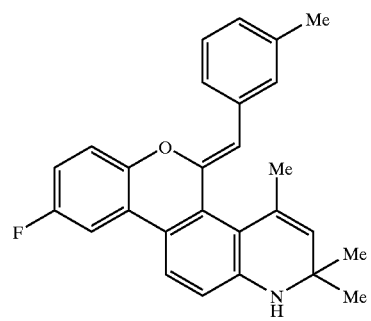

Jones, et al, described compound 3 (U.S. Pat. No. 5,696,127) as a PR ligand.

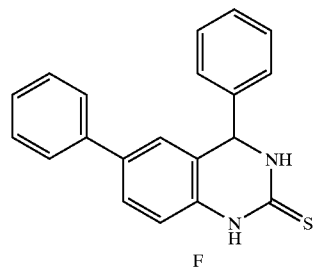

Zhi, et al, described lactones 4, 5 and 6 as PR antagonists (J. Med. Chem., 41, 291, 1998).

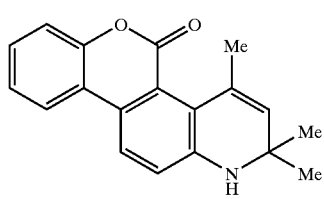

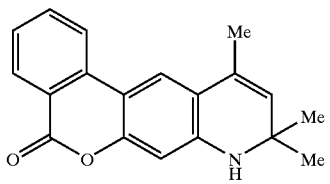

6

Zhi, et al, described the ether 7 as a PR antagonist (*J. Med. Chem.*, 41, 291, 1998).

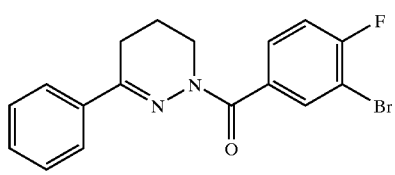

7

Combs, et al., disclosed the amide 8 as a ligand for the PR (*J. Med. Chem.*, 38, 4880, 1995).

8

Perlman, et. al., described the vitamin D analog 9 as a PR ligand (*Tet. Letters*, 35, 2295, 1994).

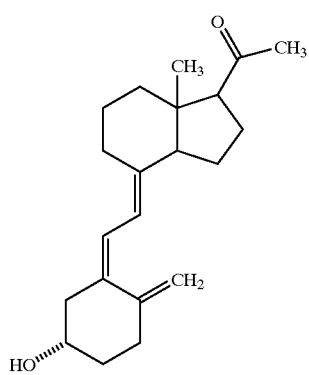

9

Hamann, et al, described the PR antagonist 10 (*Ann. N.Y. Acad. Sci.*, 761, 383, 95).

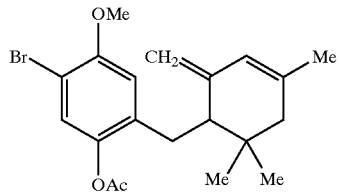

10

Chen, et al, described the PR antagonist 11 (Chen, et al, POI-37, 16$^{th}$ Int. Cong. Het. Chem, Montana, 1997).

11

Kurihari, et. al., described the PR ligand 12 (*J. Antibiotics*, 50, 360, 1997).

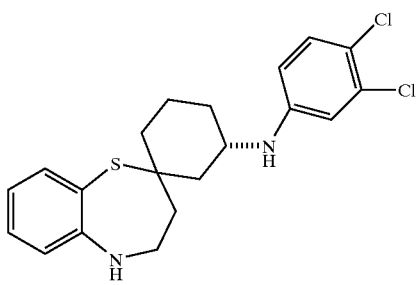

12

A number of publications reported the synthesis and utilities of benzodiazinones and benzoxazines. Included in this literature is the patent by Kubla et al. (U.S. Pat. No. 4,666,913) which claimed that the compound such as A and B could be used as cardiotonic agents. Ning et al. reported the synthesis of quinazolinones such as C.

Gromachevskaya et al. (*Chem. Heterocycl. Compd.* (N.Y.), 33(10), 1209–1214 (1998)) studied the bromination process of certain benzoxazines such as compound D. Kobzina et al. (U.S. Pat. No. 3,917,592) claimed that compounds such as E can be used as a herbicidal agent.

D

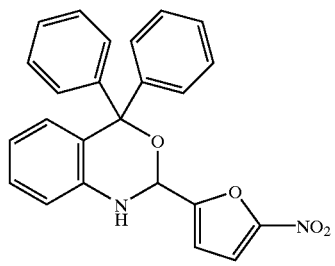

-continued

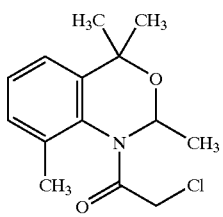

E

Pflegel et al. (Pharmazie, 37(10), 714–717(1982)) disclosed quinazolin-2-thiones such as compound F in their study of polarography of heterocyclics. No activity of the compound F was mentioned.

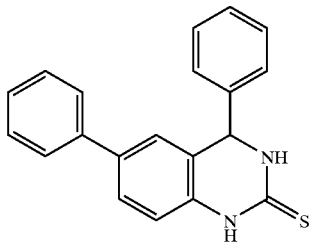

F

U.S. Pat. No. 5,521,166 (Grubb) teaches cyclophasic hormonal regimens comprising an antiprogestin and a progestin wherein the progestin is administered in the alternating presence and absence of an antiprogestin. The disclosed regimens also provide for use of an estrogen for a period of from 2–4 days to prevent breakthrough bleeding.

DESCRIPTION OF THE INVENTION

This invention provides combination therapies and dosing regimens utilizing antiprogestational agents in combination with one or more progestational agents. This invention further provides methods of treatment and dosing regimens further utilizing in combination with these antiprogestins and progestins, an estrogen, such as ethinyl estradiol.

These regimens and combinations may be administered to a mammal to induce contraception or for the treatment and/or prevention of secondary amenorrhea, dysfunctional bleeding, uterine leiomyomata, endometriosis, polycystic ovary syndrome, carcinomas and adenocarcinomas of the endometrium, ovary, breast, colon, prostate. Additional uses of the invention include stimulation of food intake. The uses herein for the treatment and/or prevention of the conditions or diseases described above includes the continuous administration or periodic discontinuation of administration of the invention to allow for minimization of effect dose or minimization of side effects or cyclic menstrual bleeding.

The use of this invention for contraception includes administration, preferably orally, to a female of child bearing age an antiprogestin in combination with an estrogen or progestin or both. These administration regimens are preferably carried out over 28 consecutive days, with a terminal portion of the cycle containing administration of no progestins, estrogens or anti-progestins.

The progestins of these combinations may be administered alone or in combination with an estrogen for the first 14–24 days of the cycle, the progestins being administered at a dosage range equal in progestational activity to about 35 μg to about 150 μg levonorgestrel per day, preferably equal in activity to from about 35 μg to about 100 μg levonorgestrel per day. An antiprogestin may then be administered alone or in combination with an estrogen for a period of 1 to 11 days to begin on any cycle day between day 14 and 24. The anti-progestin in these combinations may be administered at a dose of from about 2 μg to about 50 μg per day and the estrogen may be administered at a dose of from about 10 μg to about 35 μg per day. In an oral administration, a package or kit containing 28 tablets will include a placebo tablet on those days when the antiprogestin or progestin or estrogen is not administered.

In a preferred embodiment of this invention, the progestins of this invention may be administered alone or in combination with estrogen for the initial 18 to 21 days of a 28-day cycle, followed by administration of an antiprogestin, alone or in combination with an estrogen, for from 1 to 7 days.

The estrogen to be used in the combinations and formulations of this invention is preferably ethinyl estradiol.

Progestational agents useful with this invention include, but are not limited to, levonorgestrel, norgestrel, desogestrel, 3-ketodesogestrel, norethindrone, gestodene, norethindrone acetate, norgestiimate, osaterone, cyproterone acetate, trimegestone, dienogest, drospirenone, nomegestrol, or (17-deacetyl)norgestirate . Among the preferred progestins for use in the combinations of this invention are levonorgestrel, gestodene and trimegestone.

Examples of orally administered regimens of this invention over a 28 day cycle include administration of a progestational agent solely for the first 21 days at a daily dose equal in progestational activity to from about 35 to about 100 μg of levonorgestrel. An antiprogestin compound of this invention may then be administered at a daily dose of from about 2 to 50 mg from day 22 to day 24, followed by no administration or administration of a placebo for days 25 to 28. It is most preferred that the daily dosages of each relevant active ingredient be incorporated into a combined, single daily dosage unit, totaling 28 daily units per 28-day cycle.

In another regimen, a progestational agent may be coadministered for the first 21 days at a daily dose equal in progestational activity to from about 35 to about 150 μg levonorgestrel, preferably equal in activity to from about 35 to about 100 μg levonorgestrel, with an estrogen, such as ethinyl estradiol, at a daily dose range of from about 10 to about 35 μg. This may be followed as described above with an antiprogestin administered at a daily dose of from about 2 to 50 mg from day 22 to day 24, followed by no administration or administration of a placebo for days 25 to 28.

Still another regimen within the scope of this invention will include coadministration from days 1 to 21 of a progestational agent, the progestational agent, preferably levonorgestrel, being administered at a daily dose equal in progestational activity to from about 35 to about 100 μg levonorgestrel, and an estrogen, such as ethinyl estradiol, at a daily dose range of from about 10 to about 35 μg. This will be followed on days 22 to 24 by coadministration of an antiprogestin (2 to 50 mg/day) and an estrogen, such as ethinyl estradiol, at a daily dose of from about 10 to about 35 μg. From day 25 to day 28, this regimen may be followed by no administration or administration of a placebo.

This invention also kits or packages of pharmaceutical formulations designed for use in the regimens described herein. These kits are preferably designed for daily oral administration over a 28-day cycle, preferably for one oral administration per day, and organized so as to indicate a single oral formulation or combination of oral formulations to be taken on each day of the 28-day cycle. Preferably each kit will include oral tablets to be taken on each the days specified, preferably one oral tablet will contain each of the combined daily dosages indicated.

According to the regimens described above, one 28-day kit may comprise.

a) an initial phase of from 14 to 21 daily dosage units of a progestational agent equal in progestational activity to about 35 to about 150 μg levonorgestrel, preferably equal in progestational activity to about 35 to about 100 μg levonorgestrel;

b) a second phase of from 1 to 11 daily dosage units of an antiprogestin compound of this invention, each daily dosage unit containing an antiprogestin compound at a daily dosage of from about 2 to 50 mg; and c) optionally, a third phase of an orally and pharmaceutically acceptable placebo for the remaining days of the cycle in which no antiprogestin, progestin or estrogen is administered.

A preferred embodiment of this kit may comprise:

a) an initial phase of 21 daily dosage units of a progestational agent equal in progestational activity to about 35 to about 150 μg levonorgestrel, preferably equal in progestational activity to about 35 to about 100 μg levonorgestrel;

b) a second phase of 3 daily dosage units for days 22 to 24 of an antiprogestin compound of this invention, each daily dosage unit containing an antiprogestin compound at a daily dosage of from about 2 to 50 mg; and c) optionally, a third phase of 4 daily units of an orally and pharmaceutically acceptable placebo for each of days 25 to 28.

Another 28-day cycle packaging regimen or kit of this invention comprises:

a) a first phase of from 18 to 21 daily dosage units of a progestational agent equal in progestational activity to about 35 to about 150 μg levonorgestrel, preferably equal in activity to from about 35 to about 100 μg levonorgestrel, and, as an estrogen, ethinyl estradiol at a daily dose range of from about 10 to about 35 μg; and b) a second phase of from 1 to 7 daily dosage units of an antiprogestin of this invention at a daily dose of from about 2 to 50 mg; and c) optionally, an orally and pharmaceutically acceptable placebo for each of the remaining 0–9 days in the 28-day cycle in which no progestational agent, estrogen or antiprogestin is administered.

A preferred embodiment of the kit described above may comprise:

a) a first phase of 21 daily dosage units of a progestational agent equal in progestational activity to about 35 to about 150 μg levonorgestrel, preferably equal in activity to from about 35 to about 100 μg levonorgestrel, and, as an estrogen, ethinyl estradiol at a daily dose range of from about 10 to about 35 μg; and b) a second phase of 3 daily dosage units for days 22 to 24 of an antiprogestin administered at a daily dose of from about 2 to 50 mg; and c) optionally, a third phase of 4 daily dose units of an orally and pharmaceutically acceptable placebo for each of days 25 to 28.

A further 28-day packaged regimen or kit of this invention comprises:

a) a first phase of from 18 to 21 daily dosage units, each containing a progestational agent of this invention at a daily dose equal in progestational activity to about 35 to about 150 μg levonorgestrel, preferably equal in activity to from about 35 to about 100 μg levonorgestrel, and ethinyl estradiol at a daily dose range of from about 10 to about 35 μg, b) a second phase of from 1 to 7 daily dose units, each daily dose unit containing an antiprogestin of this invention at a concentration of from 2 to 50 mg; and ethinyl estradiol at a concentration of from about 10 to about 35 μg; and c) optionally, an orally and pharmaceutically acceptable placebo for each of the remaining 0–9 days in the 28-day cycle in which no progestational agent, estrogen or antiprogestin is administered.

A preferred embodiment of the package or kit just described comprises:

a) a first phase of 21 daily dosage units, each containing a progestational agent of this invention at a daily dose equal in progestational activity to about 35 to about 150 μg levonorgestrel, preferably from about 35 to about 100 μg levonorgestrel, and ethinyl estradiol at a daily dose range of from about 10 to about 35 μg;

b) a second phase of 3 daily dose units for days 22 to 24, each dose unit containing an antiprogestin of this invention at a concentration of from 2 to 50 mg; and ethinyl estradiol at a concentration of from about 10 to about 35 μg and c) optionally, a third phase of 4 daily units of an orally and pharmaceutically acceptable placebo for each of days 25 to 28.

In each of the regimens and kits just described, it is preferred that the daily dosage of each pharmaceutically active component of the regimen remain fixed in each particular phase in which it is administered. It is also understood that the daily dose units described are to be administered in the order described, with the first phase followed in order by the second and third phases. To help facilitate compliance with each regimen, it is also preferred that the kits contain the placebo described for the final days of the cycle. It is further preferred that each package or kit comprise a pharmaceutically acceptable package having indicators for each day of the 28-day cycle, such as a labeled blister package or dial dispenser packages known in the art.

In this disclosure, the terms anti-progestational agents, anti-progestins and progesterone receptor antagonists are understood to be synonymous. Similarly, progestins, progestational agents and progesterone receptor agonists are understood to refer to compounds of the same activity.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

Compounds of this invention which may be used as the anti-progestational agents in the kits, methods and regimens herein are those of the Formula I:

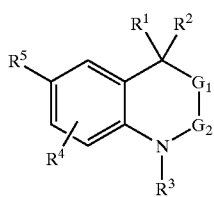

wherein:
R¹, R² are independent substituents selected from the group which includes H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

or R¹ and R² are fused to form:
a) an optionally substituted 3 to 8 membered spirocyclic alkyl ring;
b) an optionally substituted 3 to 8 membered spirocyclic alkenyl; or
c) an optionally substituted 3 to 8 membered heterocyclic ring containing one to three heteroatoms from the group including O, S and N; the spirocyclic rings of a), b) and c) being optionally substituted by from 1 to 4 groups selected from fluorine, $C_1$ to $C_6$ alkyl, $C_1$ to $C_6$ alkoxy, $C_1$ to $C_6$ thioalkyl, —$CF_3$, —OH, —CN, $NH_2$, —NH($C_1$ to $C_6$ alkyl), or —N($C_1$ to $C_6$ alkyl)$_2$;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, substituted $C_1$ to $C_3$ aminoalkyl, $R^B$ is H, $C_1$ to $C_3$ alkyl, substituted $C_1$ to $C_3$ alkyl, R³ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, or substituted alkynyl, $COR^C$, $R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, substituted $C_1$ to $C_3$ aminoalkyl, R⁴ is H, halogen, CN, $NO_2$, $C_1$ to $C_6$ alkyl, substituted $C_1$ to $C_6$ alkyl, alkynyl, or substituted alkynyl, $C_1$ to $C_6$ alkoxy, substituted $C_1$ to $C_6$ alkoxy, amino, $C_1$ to $C_6$ aminoalkyl, substituted $C_1$ to $C_6$ aminoalkyl, R⁵ is a trisubstituted benzene ring containing the substituents X, Y and Z as shown below,

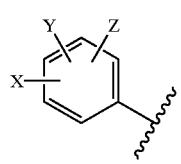

X is taken from the group including halogen, CN, $C_1$ to $C_3$ alkyl, substituted $C_1$ to $C_3$ alkyl, alkynyl, or substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing 1 to 3 heteroatoms, $COR^D$, $OCOR^D$, or $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, substituted $C_1$ to $C_3$ alkyl;

Y and Z are independent substituents taken from the group including H, halogen, CN, $NO_2$, amino, aminoalkyl, $C_1$ to $C_3$ alkoxy, $C_1$ to $C_3$ alkyl, or $C_1$ to $C_3$ thioalkoxy; or R⁵ is a five or six membered ring with 1, 2, or 3 heteroatoms from the group including O, S, SO, $SO_2$ or $NR^6$ and containing one or two independent substituents from the group including H, halogen, CN, $NO_2$, amino, and $C_1$ to $C_3$ alkyl, $C_1$ to $C_3$ alkoxy, $C_1$ to $C_3$ aminoalkyl, $COR^F$, or $NR^G COR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

R⁶ is H or $C_1$ to $C_3$ alkyl;

$G_1$ is O, $NR_7$, or $CR_7R_8$;

$G_2$ is CO or $CR_7R_8$;

provided that when $G_1$ is O, $G_2$ is $CR_7R_8$, and $G_1$ and $G_2$ cannot both be $CR_7R_8$;

$R_7$ and $R_8$ are independent substituents selected from H or an optionally substituted alkyl, aryl, or heterocyclic moiety;

or pharmaceutically acceptable salt thereof

Preferred antiprogestin compounds of this invention include those of Formula I:

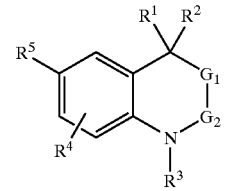

wherein:
R¹ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

R² is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$; or R¹ and R² are fused to form an optionally substituted 3 to 8 membered spirocyclic alkyl, alkenyl or heterocyclic ring containing one to three heteroatoms from the group including O, S and N, as described above;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl,

R³ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, or substituted alkynyl, $COR^C$;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, amino, $C_1$ to $C_6$ aminoalkyl, substituted $C_1$ to $C_6$ aminoalkyl, $R^5$ is a trisubstituted benzene ring containing the substituents X, Y and Z as shown below:

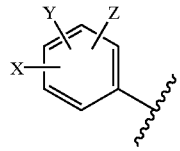

X is selected from halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 membered heterocyclic ring containing 1 to 3 heteroatoms, $COR^D$, $OCOR^D$, or $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents taken from the group including H, halogen, CN, $NO_2$, $C_1$ to $C_3$ alkoxy, $C_1$ to $C_3$ alkyl, or $C_1$ to $C_3$ thioalkoxy; or $R^5$ is a five or six membered ring with 1, 2, or 3 heteroatoms from the group including O, S, SO, $SO_2$ or $NR^6$ and containing one or two independent substituents from the group including H, halogen, CN, $NO_2$ amino, and $C_1$ to $C_3$ alkyl, $C_1$ to $C_3$ alkoxy;

$R^6$ is H, or $C_1$ to $C_3$ alkyl.

$G_1$ is O, $NR_7$, or $CR_7R_8$ $G_2$ is CO or $CR_7R_8$, with the proviso that when $G_1$ is O, $G_2$ is $CR_7R_8$, and $G_1$ and $G_2$ cannot both be $CR_7R_8$;

wherein $R_7$ and $R_8$ are independent substituent selected from H, alkyl, substituted alkyl, aryl, substituted aryl, heterocyclic, or substituted heterocyclic or a pharmaceutically acceptable salt thereof.

Still, more preferred antiprogestin compounds include those of the formula:

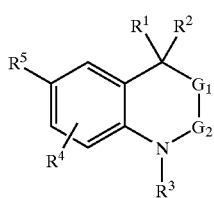

wherein:

$R^1 = R^2$ and are selected from $C_1$ to $C_3$ alkyl, substituted $C_1$ to $C_3$ alkyl, or spirocyclic alkyl constructed by fusing $R^1$ and $R^2$ to form a 3 to 6 membered spirocyclic ring;

$R^3$ is H, OH, $NH_2$, $C_1$ to $C_6$ alkyl, substituted $C_1$ to $C_6$ alkyl, —COH, —CO($C_1$ to $C_4$ alkyl) or —CO($C_1$ to $C_4$ alkoxy);

$R^4$ is H, halogen, $NO_2$, $C_1$ to $C_3$ alkyl, substituted $C_1$ to $C_3$ alkyl, $R^5$ is a disubstituted benzene ring containing the substituents X, and Y as shown below

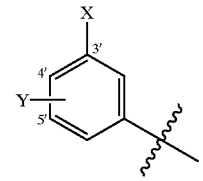

X is taken from the group including halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, $C_1$ to $C_3$ thioalkoxy, Y is a substituent on the 4' or 5' position from the group including H, halogen, CN, $NO_2$, $C_1$ to $C_3$ alkoxy, $C_1$ to $C_4$ alkyl, $C_1$ to $C_3$ thioalkoxy or $R^5$ is a five membered ring with the structure shown below

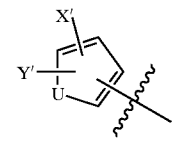

U is O, S, or $NR^6$, $R^6$ is H, or $C_1$ to $C_3$ alkyl, $C_1$ to $C_4$ $CO_2$alkyl, X' is from the group including halogen, CN, $NO_2$, $C_1$ to $C_3$ alkyl and $C_1$ to $C_3$ alkoxy Y' is from the group including H and $C_1$ to $C_4$ alkyl or $R^5$ is a six membered ring with the structure shown

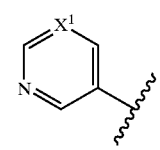

$X^1$ is N or $CX^2$, $X^2$ is halogen, CN, alkoxy, or $NO_2$, $G_1$ is O, $NR_7$, or $CR_7R_8$ $G_2$ is CO or $CR_7R_8$ provided that when $G_1$ is O, $G_2$ is $CR_7R_8$, and $G_1$ and $G_2$ cannot both be $CR_7R_8$;

wherein $R_7$ and $R_8$ are independent substituents selected from H, alkyl, substituted alkyl, aryl, substituted aryl, heterocyclic, or substituted heterocyclic;

or pharmaceutically acceptable salt thereof.

Still, other preferred antiprogestin compounds are those of Formula I

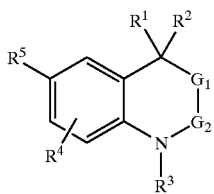

wherein:
R$^1$=R$^2$ and are selected from the group which includes CH$_3$ and spirocyclic alkyl constructed by fusing R$^1$ and R$^2$ to form a 6 membered spirocyclic ring,
R$^3$ is H, OH, NH$_2$, CH$_3$, substituted methyl, COR$^C$,
R$^C$ is H, C$_1$ to C$_3$ alkyl, C$_1$ to C$_4$ alkoxy,
R$^4$ is H, halogen, C$_1$ to C$_3$ alkyl,
R$^5$ is a disubstituted benzene ring containing the substituents X, and Y as shown below

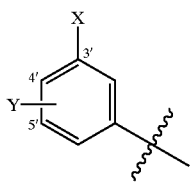

X is taken from the group including halogen, CN, methoxy, NO$_2$, 2-thiazole,
Y is a substituent on the 4' or 5' position from the group including H and F, or
R$^5$ is a five membered ring with the structure shown below

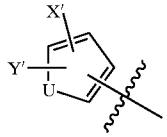

U is O, S, or NH,
X' is from the group including halogen, CN, NO$_2$,
Y' is from the group including H and C$_1$ to C$_4$ alkyl
G$_1$ is O, NR$_7$, or CR$_7$R$_8$
G$_2$ is CO or CR$_7$R$_8$
provided that when G$_1$ is O, G$_2$ is CR$_7$R$_8$, and G$_1$ and G$_2$ cannot both be CR$_7$R$_8$;
R$_7$ and R$_8$ are independent substituent selected from H, alkyl, substituted alkyl, aryl, substituted aryl, heterocyclic, or substituted heterocyclic;
and pharmaceutically acceptable salts thereof.

The antiprogestin compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof It will be understood by one skilled in the art that the number of substituents listed for spirocyclic or heterospirocyclic rings formed by fusing R$_1$ and R$_2$ will be determined by the size of the spirocyclic ring.

The term "alkyl" is used herein to refer to both straight- and branched-chain saturated aliphatic hydrocarbon groups having one to eight carbon atoms; "alkenyl" is intended to include both straight- and branched-chain alkyl groups with at least one carbon—carbon double bond and two to eight carbon atoms; "alkynyl" group is intended to cover both straight- and branched-chain alkyl groups with at least one carbon—carbon triple bond and two to eight carbon atoms.

The terms "substituted alkyl", "substituted alkenyl", and "substituted alkynyl" refer to alkyl, alkenyl, and alkynyl as just described having one or more substituents from the group including halogen, CN, OH, NO$_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of an alkyl, alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include but are not limited to phenyl, naphthyl, biphenyl, anthryl, tetrahydronaphthyl, phenanthryl.

The term "substituted aryl" refers to an aryl as just defined having one to four substituents from the group including halogen, CN, OH, NO$_2$, amino, alkyl, cycloalkyl, alkenyl, alkynyl, alkoxy, aryloxy, substituted alkyloxy, alkylcarbonyl, alkylcarboxy, alkylamino, or arylthio.

The term "aryl" is used herein to refer to an aromatic system which may be a single ring or multiple aromatic rings fused or linked together as such that at least one part of the fused or linked rings forms the conjugated aromatic system. The aryl groups include but are not limited to phenyl, naphthyl, biphenyl, anthryl, tetrahydronaphthyl, phenanthryl.

The term "substituted aryl" refers to aryl as just defined having one to four substituents from the group including halogen, CN, OH, NO$_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having one to four substituents selected from the group which includes halogen, CN, OH, NO$_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "alkoxy" refers to the OR group, where R is alkyl or substituted alkyl. The term "aryloxy" is used herein to indicate the OR group, where R is aryl or substituted aryl. The term "alkylcarbonyl" refers to the RCO group, where R is alkyl or substituted alkyl. The term "alkylcarboxy" refers to the COOR group, where R is alkyl or substituted alkyl. The term "aminoalkyl" refers to both secondary and tertiary amines wherein the alkyl or substituted alkyl groups, containing one to eight carbon atoms, which may be either same or different and the point of attachment is on the nitrogen atom The term "halogen" refers to Cl, Br, F, and I element.

The antiprogestin compounds of this invention can be prepared following the Schemes illustrated below:

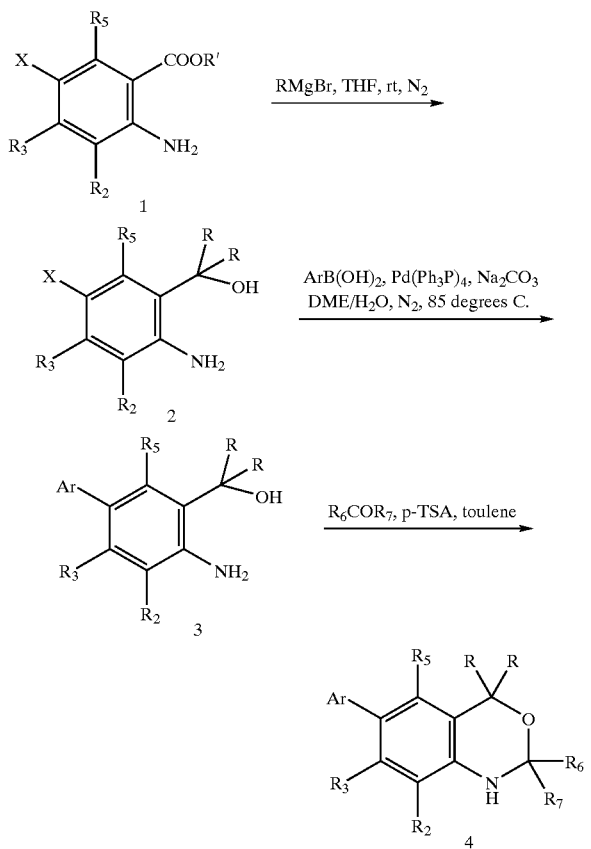

As demonstrated in Scheme I, the anti-progestational compounds of this invention are generally prepared by employing the suitable coupling reaction as a key step. An appropriately substituted ortho-amino benzoic acid or its derivatives such as ethyl ester (X=Br, I, Cl, or a latent coupling precursor such as alkoxy group which can be converted into OTf group suitable in the coupling reaction.) was treated with a suitable organo metallic reagent, e.g. Grignard reagent, in appropriate nonprotic solvents which include but not limited to THF or ether to give ortho-amino carbinol 2 under an inert atmosphere such as argon or nitrogen at −78° C. to room temperature. The arylation of amino carbinol 2 to yield 3 can be effected by various coupling reactions including Suzuki, Stille reactions. These reactions are commonly performed in the presence of a transition metallic catalyst, e.g., palladium or nickel complex often with phosphino ligands, e.g., Ph₃P, dppf, dppe or a catalyst such as palladium acetate. Under this catalytic condition, an appropriately substituted nucleophilic reagent, e.g., aryl boronic acid, arylstannane, or aryl zinc compound, is coupled with amino carbinol 2 to give 3. If a base is needed in the reaction, the commonly used bases include but not limited to sodium bicarbonate, sodium carbonate, potassium phosphate, barium carbonate, cesium fluoride, or potassium acetate. The most commonly used solvents in these reactions include benzene, DMF, isopropanol, ethanol, DME, ether, acetone, or a mixture of above solvent and water. The coupling reaction is generally executed under an inert atmosphere such as nitrogen or argon at temperatures ranging from room temperature to 95° C. The compounds of this invention 4 can be effected by treatment of amino carbinol 3 with an appropriate ketone in the presence of an suitable acid catalyst such as p-toluenesulfonic acid in a suitable solvent such as toluene, benzene under an inert atmosphere such as argon or nitrogen at room temperature to reflux.

Scheme II describes the procedure to prepare benzoxazines bearing two different substituents at position-4. The Weinreb amide 6 can be prepared from an appropriately substituted isatoic anhydride 5 when treated with N-, O-dimethylhydroxyl-amine hydrochloride salt in a protic solvent such as ethanol, or isopropanol at reflux under an inert atmosphere such as argon or nitrogen. Coupling of amide 6 with an aryl electrophile such as aryl boronic acid or arylstannane to give 7 can be effected by employing a typical coupling reaction such as Suzuki, Stille coupling procedure in a similar fashion as described for the preparation of compound 3. Treatment of Weinreb amide 7 with organo metallic compounds, e.g., alkyllithium, alkynyllithium, aryllithium, or their Grignard counterpart in a nonprotic solvent such as THF or ether under an inert atmosphere such as argon or nitrogen at −78° to room temperature affords amino ketone 8. Conversion of ketone 8 to carbinol 9 can be effected by treatment of 8 with an organo metallic reagent such as alkyl, alkynyl, or aryl Grignard reagent in a nonprotic solvent such as THF or ether under an inert atmosphere such as argon or nitrogen at −78° C. to room temperature. Conversion of ketone 8 to carbinol 9 can also be effected by reduction of ketone group of 8 to the carbinol moiety of 9 using an appropriate reducing reagent such as lithium aluminum hydride, sodium borohydride in a suitable solvent such as THF, ether, or anhydrous alcohol under an inert atmosphere in the temperature ranging from 0° C. to the boiling point of the solvent. Further conversion of 9 to the compounds of this invention can be effected as described in scheme I for the preparation of compound 4.

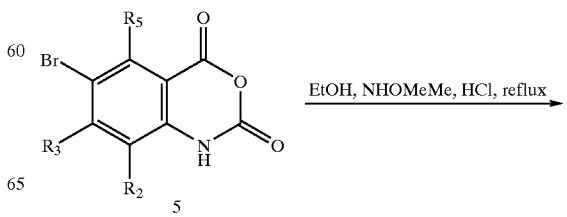

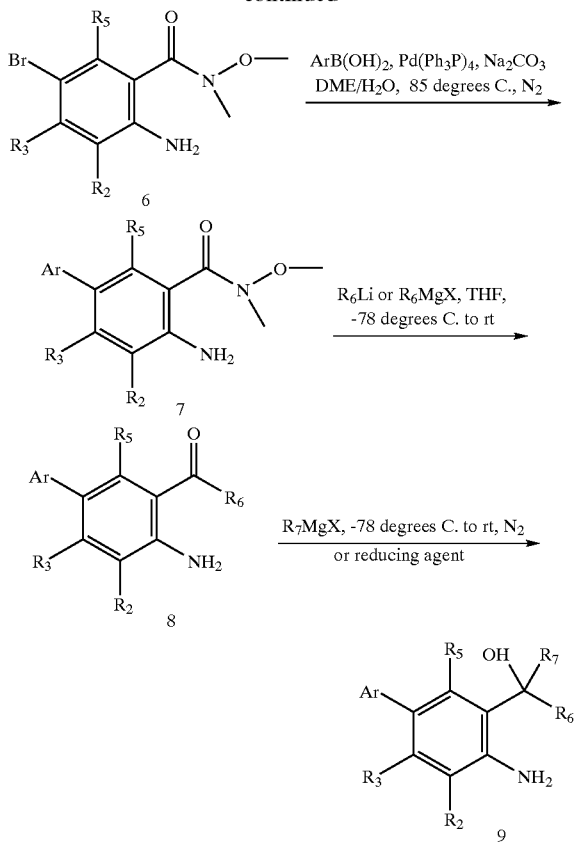

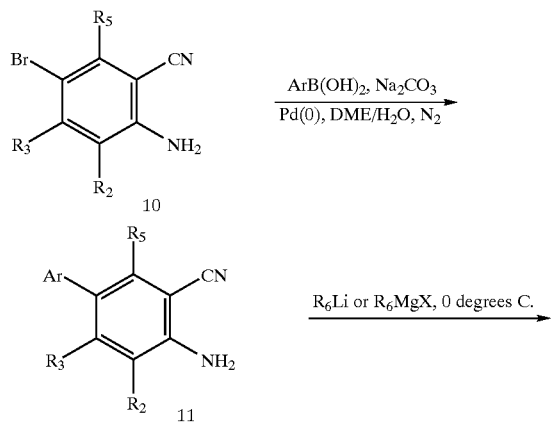

Alternatively, ortho-amino ketone 8 can be prepared by treatment of ortho-amino benzonitrile 11 with an organo metallic compound such as organo lithium reagent or Grignard reagent in a suitable solvent such as THF or ether under an inert atmosphere such as argon or nitrogen at temperatures ranging from −78° C. to room temperature as illustrated in Scheme 111. Benzonitrile 11 can be readily prepared from an appropriately substituted benzonitrile such as bromobenzonitrile 10 using a suitable coupling reaction such as Stille or Suzuki protocol carried out in a similar fashion as described for the preparation of the Weinreb amide 7.

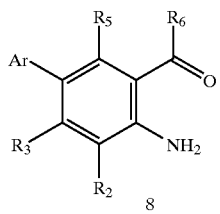

Scheme IV illustrates the synthesis of 3,4-dihydroquinazolin-2-ones. The substituted 2-aminobenzonitrile 11 is treated with an organo metallic compound such as organo lithium or Grignard reagent in a nonprotic solvent such as THF or ether under an inert atmosphere such argon or nitrogen at −78° C. to room temperature to produce an imino intermediate which is reacted with a suitable carbonate such as diethyl carbonate or dimethyl carbonate in situ at 0° C. to 60° C. to give quinazolin-2-ones 12. Protection of quinazolin-2-ones 12 with a suitable protective group such as para-methoxybenzyl moiety can be effected by treating 12 with a suitable base such as potassium hydride, potassium t-butoxide, or sodium hydride followed by addition of a protective reagent such as para-methoxybenzyl chloride in an appropriate solvent such as DMF, or a mixture of solvents such as THF and DMF under an inert atmosphere such as nitrogen or argon at 0° C. to room temperature. The Michael addition of a suitable organo metallic compound such as organo lithium or Grignard reagent to the protected quinazohin-2-ones 12 to give 13 can be accomplished in the presence of a suitable Lewis acid such as magnesium triflate in a nonprotic solvent such as THF or ether under an inert atmosphere such as argon or nitrogen at 0° C. to room temperature.

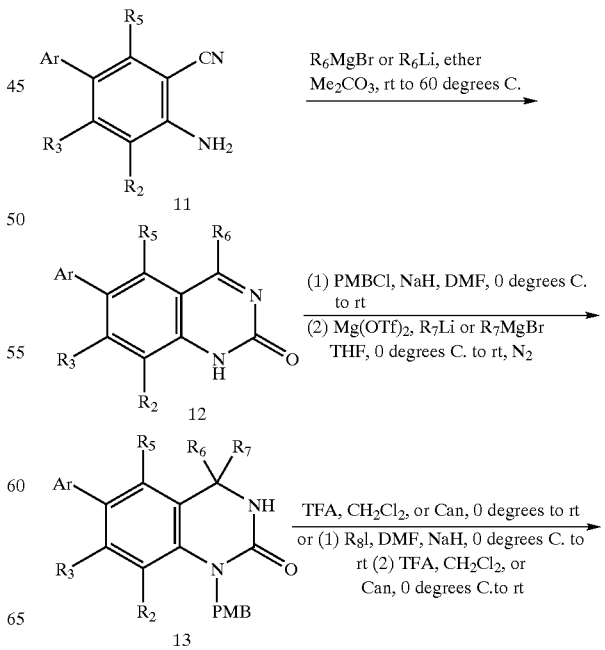

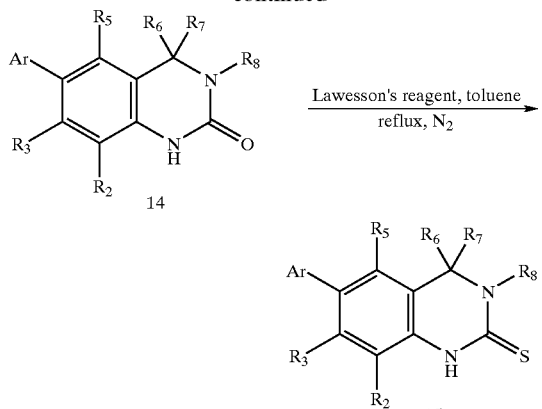

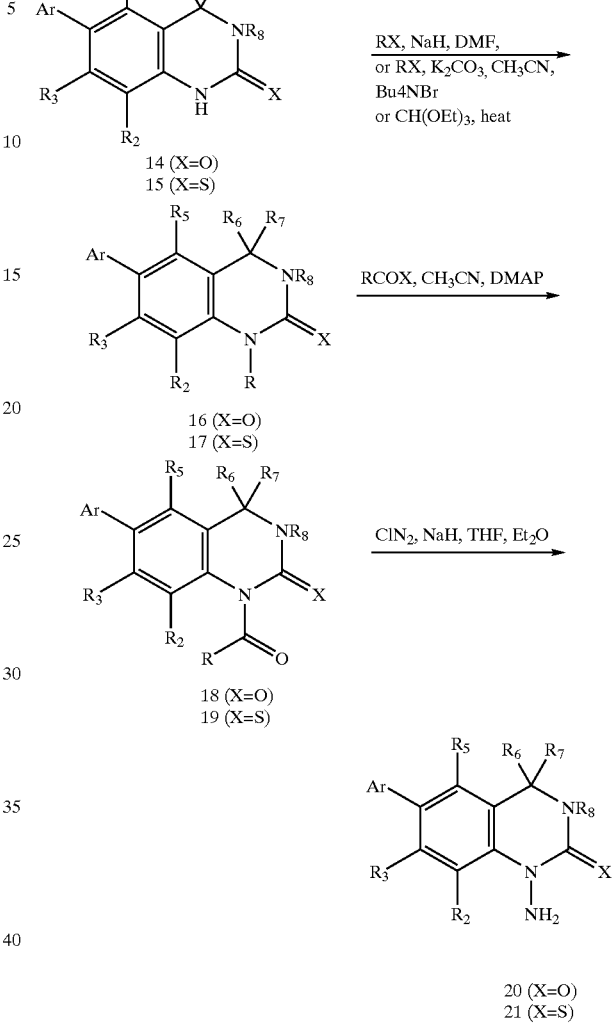

Removal of protective group can be effected by treating 13 with a suitable deprotecting reagent, e.g. for the para-methoxybenzyl protective group it can be removed by treatment of 13 with protic acid such as TFA or with Ceric ammonium nitrate in a suitable solvent such as methylene chloride at 0° C. to room temperature under an inert atmosphere such as argon or nitrogen. Prior to the removal of protective group, the alkylation of 3-nitrogen can be achieved by treating 13 with an appropriate base such as sodium hydride, potassium hydride, or potassium t-butoxide in a suitable solvent such as DMF followed by quenching the reaction solution with an organo iodide or an organo triflate such as iodomethane under an inert atmosphere such as argon or nitrogen at 0° C. to room temperature. The compounds of the present invention 14 can be accomplished when the protective group is removed with a suitable reagent, e.g. for the para-methoxybenzyl protective group it can be removed by treatment of 13 with protic acid such as TFA or with Ceric ammonium nitrate in a suitable solvent such as methylene chloride at 0° C. to room temperature under an inert atmosphere such as argon or nitrogen.

The conversion of compounds 14 to 3,4-dihydroquinazolin-2-thiones 15 can be accomplished by treatment of 14 with a suitable sulfur reagent such as Lawesson's reagent in a nonprotic solvent such as o-xylene, chlorobenzene, or toluene under an inert atmosphere such as argon or nitrogen at reflux.

As illustrated in scheme V, the compounds 14 or 15 can be further derivatized at position-1 via numerous approaches leading to a variety of the novel derivatives including 1-alkyl, substituted 1-alkyl, 1-carbonyl, substituted 1-carbonyl, 1-carboxy, substituted 1-carboxy derivatives. For examples, alkyl or substituted alkyl derivatives 16 or 17 can be effected by treatment of carbamate 14 or 15 with a suitable base such as sodium hydride in a suitable solvent such as DMF under an inert atmosphere such as argon or nitrogen followed by addition of an appropriate electrophile such as alkyl or substituted alkyl bromide, iodide, or triflate. Such transformation of 14 or 15 to 16 or 17 at position-1 can also be effected using biphasic condition as indicated in scheme V in which alkylation is executed using a biphasic catalyst such as tributylammonium bromide in a suitable solvent such as acetonitrile. A further example of such modification in position-i includes but not limited to the one depicted in scheme V in that heating of 14 or 15 with triethyl orthoformate affords I-substituted derivatives of compound 14 or 15.

The acylation or carboxylation of the compound 14 or 15 at position-1 to give compound 18 or 19 can be readily effected by treatment of 14 or 15 with a suitable acylating or carboxylating reagent such as di-t-butyl dicarbonate in the presence of a suitable basic catalyst such as DMAP in a suitable solvent such as acetonitrile under an inert atmosphere such as argon or nitrogen. The amination of position-1 of compound 14 or 15 to give compounds 20 and 21 can be furnished using a suitable aminating reagent such as chloroamine in the presence of a suitable base such as sodium hydride in a suitable solvent such as THF or diethyl ether following the literature procedure (Metlesics et al. *J. Org. Chem.* 30, 1311(1965)).

According to scheme VI an appropriate aniline such as 4-bromoaniline 22, is reacted in the presence of a base in a suitable nonprotic solvent with an acryloyl chloride 23 to form the amide 24. The base is preferably a strong base such as sodium hydride or sodium or potassium hexamethyldisilylamide, utilizing THF as the solvent under an inert atmosphere (nitrogen or argon) from 0° C. up to the reflux temperature of the solvent.

Scheme VI

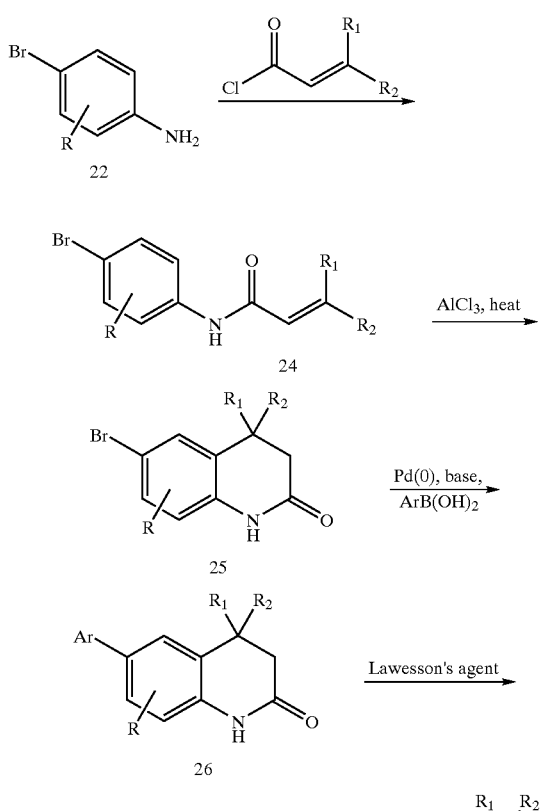

Scheme VII

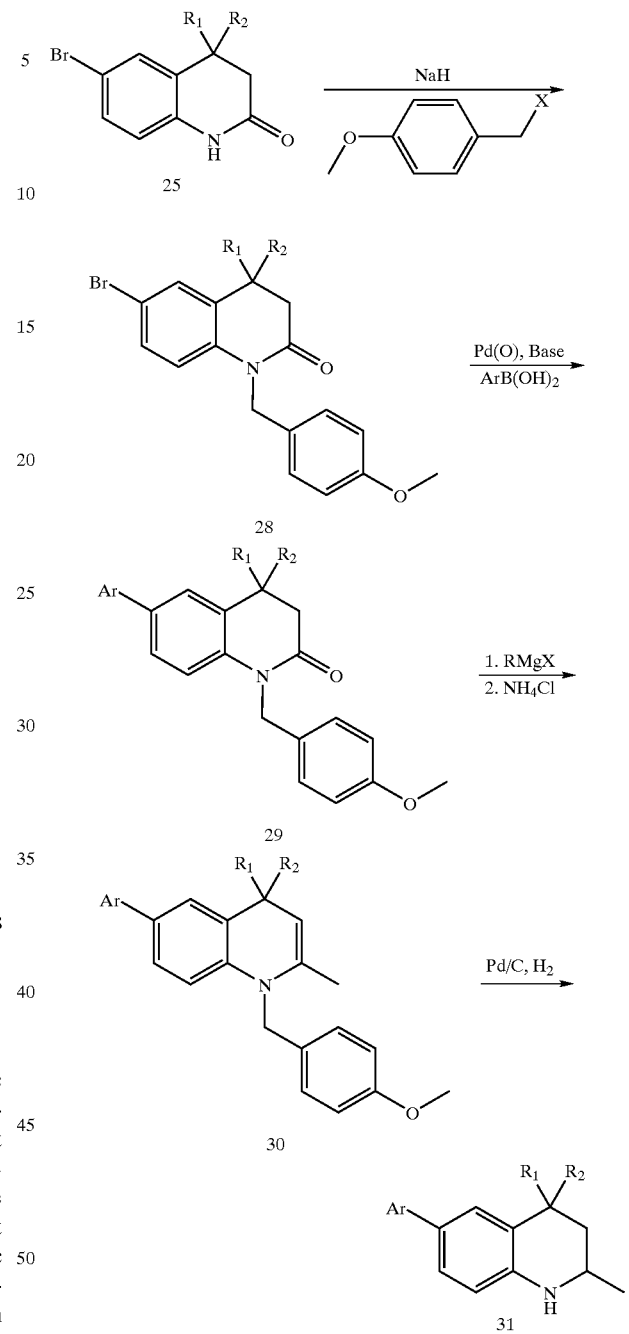

Reaction of the amide 24 under strongly acidic conditions, sulfuric acid, borontrifluoride etherate, or preferably aluminum chloride either as a melt, or in an inert solvent (dichlorobenzenes) under an inert atmosphere (nitrogen or argon) from 0° C. up to the reflux temperature of the solvent then provides the cyclic amide 25. Subsequent reaction of compound 25 with an aryl or heteroaryl boronic acid, boronic acid anhydride or trialkyl stannane then provides access to the desired biaryl compound 26. The reaction can be carried out in a solvent such as acetone, ethanol, benzene, toluene or THF, under an inert atmosphere (nitrogen or argon) from 0° C. up to the reflux temperature of the solvent, in the presence of a palladium catalyst such as tetrakis(triphenylphosphine) palladium (0) or palladium acetate and may require an additive such as sodium carbonate, cesium fluoride or potassium phosphate.

The conversion of compounds 26 to thioamide 27 can be accomplished by treatment of 26 with a suitable sulfur reagent such as Lawesson's reagent in a nonprotic solvent, such as o-xylene, chlorobenzene, or toluene under an inert atmosphere such as argon or nitrogen at reflux.

According to scheme VII, an appropriate cyclic amide such as 25, is allowed to react with NaH in THF to form the anion species and then a benzyl halide is added to convert the starting material to the N-protected amide product, 28. Reaction of 28 with an aryl boronic acid in the presence of a palladium catalyst such as tetrakis(triphenylphosphine) palladium(0) or palladium acetate permits a coupling of the two aromatic species to yield 29. The reaction is normally carried out under biphasic conditions. That is, water is often employed along with an appropriate organic solvent, such as toluene or DMF. The palladium catalyst is typically added last and the reaction mixture is refluxed in the presence of an inert gas such as nitrogen. The product is treated with a Grignard Reagent, an alkyl magnesium halide, in THF followed by the addition of ammonium chloride solution to afford the enamine derivative 30. The reduction of the double bond in 30 and removal of the protecting group can be accomplished in a single step by catalytic reduction in a Parr Hydrogenation Apparatus using palladium on charcoal to form the target compound 31.

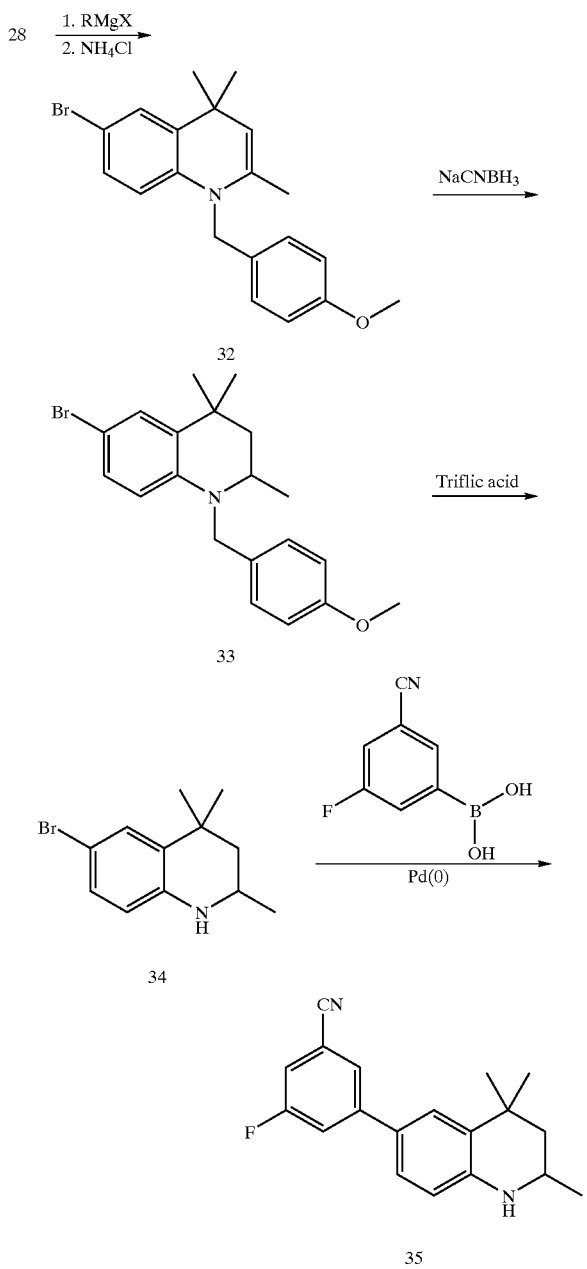

3-Fluoro-5-(2,4,4-trimethyl-1,2,3,4-hydro-qinolinyl)-benzonitrile (compound 35) can be prepared by Scheme VIII, a process sinmilar to Scheme VII. According to scheme VIII, compound 28 is allowed to react with a Grignard reagent, an alkyl magnesium halide, in THF followed by the addition of ammonium chloride solution to afford the enamine derivative 32. Reduction of the double bond with sodium cyanoborohydride affords the reduced derivative 33. Removal of the protecting group with a strong acid such as triflic or sulfuric acid affords the deprotected compound 34 which can then be coupled with a suitably substituted phenylboronic acid in the presence of a palladium catalyst such as tetrakis(triphenylphosphine)palladium(0) or palladium acetate permits a coupling of the two aromatic species to yield 35. The reaction is normally carried out under biphasic conditions. That is, water is often employed along with an appropriate organic solvent, such as toluene or DMF.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "prodrug" forms, which, when administered in such form, convert to the active moiety in vivo.

This invention includes pharmaceutical compositions and treatments which comprise administering to a mammal a pharmaceutically effective amount of one or more compounds as described above wherein $G_2$ is C=O as antagonists of the progesterone receptor. The invention further provides comparable methods and compositions which utilize one or more compounds herein wherein $G_2$ is C=S as agonists of the progesterone receptor. Moreover the invention further provides comparable methods and compositions which utilize one or more compounds herein wherein $G_1$=O and $G_2$=CR$_7$CR$_8$ are agonists of the progesterone receptor and when $G_1$=CR$_7$CR$_8$ and $G_2$=CR$_7$CR$_8$ are agonists of the progesterone receptor.

The progesterone receptor antagonists of this invention, used alone or in combination, can be utilized in methods of contraception and the treatment and/or prevention of benign and malignant neoplastic disease. Specific uses of the compounds and pharmaceutical compositions of invention include the treatment and/or prevention of uterine mryometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock. When used in contraception the progesterone receptor antagonists of the current invention may be used either alone in a continuous administration of between 1 and 500 mg per day, or alternatively used in a different regimen which would entail 2–4 days of treatment with the progesterone receptor antagonist after 21 days of a progestin, in this regimen between 0.1 and 500 mg daily doses of the progestin (e.g. levonorgestrel, trimegestone, gestodene, norethistrone acetate, norgestimate or cyproterone acetate) would be followed by between 0.1 and 500 mg daily doses of the progesterone receptor antagonists of the current invention.

The progesterone receptor antagonists of this invention, used alone or in combination, can also be utilized in methods of treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

The progesterone receptor agonists of this invention, used alone or in combination, can be utilized in methods of contraception and the treatment and/or prevention of dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake.

When used in contraception the progesterone receptor agonists of the current invention are preferably used in combination or sequentially with an estrogen agonist (e.g. ethinyl estradiol). The preferred dose of the progesterone receptor agonist is between 0.01 and 500 mg per day.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intrapenrtoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The following non-limiting examples are illustrative of the invention.

EXAMPLE 1

1-(4Amino-3'-chloro-biphenyl-3-yl)-ethanone

A mixture of 2-amino-5-bromo-N-methoxy-N-methylbenzamide (7.78 g, 30 mmol), 3-chlorophenyl boronic acid (5.63 g, 36 mmol), tetrakis(triphenylphosphine) palladium (0) (1.73 g, 1.5 mmol), and sodium carbonate (7.63 g, 72 mmol) in a mixture of DME and water (150 mL/30 mL) was degassed to remove the oxygen and was then heated at 85° C. under nitrogen for 3 hours. The reaction mixture was cooled to room temperature and treated with brine (30 mL) and ethyl acetate (100 mL). The organic layer was separated and aqueous layer was extracted with ethyl acetate (3×40 mL). The combined organic layers were washed with brine and dried with $MgSO_4$. After removal of solvent, the residue was purified by a flash chromatography (silica gel, hexane:ethyl acetate/1:1) to give 5-(3-chlorophenyl)-N-methoxy-N-methylbenzamide as a brown oil (5 g, 57%). To a solution of this benzamide (5 g, 17.2 mmol) in anhydrous THF was added in a dropwise fashion a solution of methyllithium in ether (1.4M, 28.6 mL, 40 mL) at −78° C. under nitrogen. After stirring for 30 minutes, the reaction mixture was treated with a saturated aqueous ammonium chloride solution (50 mL) at −78° C. Ethyl acetate (100 mL) was added, the organic layer was separated, and the aqueous layer was extracted with ethyl acetate (3×20 mL). The combined organic layers were washed (brine) and dried ($MgSO_4$). After removal of solvent, the residue was purified by a flash chromatography (silica gel, hexane:ethyl acetate/2:1) to afford 1-(4-amino-3'-chloro-biphenyl-3-yl)-ethanone as yellow solid (2 g, 47%): mp 89–90° C.; $^1$H-NMR ($CDCl_3$) δ 7.89 (d, 1H, J=2.0 Hz), 7.51 (m, 2H), 7.25–7.40 (m, 3H), 6.73 (d, 1H, J=8.6 Hz), 6.38 (br, 2H), 2.65 (s, 3H); MS (EI) m/z 268([M+Na]$^+$, 60%); Anal. Calc. For $C_{14}H_{12}ClNO$: C, 68.44, H, 4.92, N, 5.70. Found: C, 68.40, H, 4.89, N, 5.61.

EXAMPLE 2

1-(4Amino-3'-chloro-bithenyl-3-yl)-dimethyl-methanol

To a solution of 1-(4-amino-3'-chloro-biphenyl-3-yl)-ethanone (0.55 g, 2.2 mmol) in anhydrous THF under nitrogen was added a solution of methyl magnesium bromide (3.0 M in diethyl ether, 1 mL, 3 mmol) at 0° C. The mixture was slowly warmed to room temperature and kept stirring under nitrogen for 18 hours. The mixture was treated with 10 mL of saturated ammonium chloride aqueous solution and ethyl acetate (50 mL) was added. The organic layer was separated and the aqueous layer was extracted with ethyl acetate (3×15 mL). The combined organic layers were washed with brine (20 mL) and dried ($MgSO_4$). After removal of the solvent, the residue was purified by a flash chromatography (silica gel, hexane: ethyl acetate/2:1) to afford the title compound as an off-white solid: 186–188° C. (HCl salt). Anal. Calc. For $C_{15}H_{17}Cl_2NO$: C, 60.42, H, 5.75, N, 4.7. Found: C, 60.51, H, 5.62, N, 4.56.

EXAMPLE 3

6(3-Chloro-phenyl)-2,4,4-trimethyl-2-trifluoromethyl-1,4-dihydro-2H-benzo[d][1,3] oxazine A mixture of (4-amino-3-chloro-biphenyl-3-yl)-dimethylmethanol (0.25 g, 0.95 mmol), trifluoromethylacetone (0.16 g, 1.43 mmol), and p-toluenesulfonic acid (0.01 g, 0.05 mmol) in dry toluene (5 mL) was stirred under a blanket of nitrogen for 48 hours. Upon completion of the reaction, the toluene was removed and the residue purified via flash chromatography (silica gel, 10% ethyl acetate/hexane) to give 6-(3-chloro-phenyl)-2,4,4-trimethyl-2-trifluoromethyl-1,4-dihydro-2H-benzo[d][1,3]-oxazine (0.22 g, 65%) as a clear oil. The oil was dissolved in ether at −78° C. and then treated with a solution of 1N HCl in ether to give the hydrochloride salt of the title compound as a white solid: $^1$H-NMR (DMSO-d$_6$) δ 7.67 (bs, 1H), 7.58 (d, 1H, J=7.88 Hz), 7.42 (m, 3H), 7.32 (d, 1H, J=7.96 Hz), 6.84 (d, 1H, J=8.03 Hz), 1.52 (s, 3H), 1.5 (s, 6H); MS (APCI) m/z 354 ([M−H]$^-$, 100%); Anal. Calc. For C$_{18}$H$_{17}$ClF$_3$NO: C, 55.12; H, 4.62; N, 3.57. Found: C, 54.97; H, 4.59; N, 3.41.

EXAMPLE 4

6-(3-Chloro-phenyl)-2,2,4,4-tetramethyl-1,4-dihydro-2H-benzo[d][1,3]oxazine A mixture of (4-amino-3-chloro-biphenyl-3-yl)-dimethyl-methanol (0.46 g, 1.8 mmol), acetone (0.16 g, 2.7 mmol), and p-toluenesulfonic acid (0.017 g, 0.09 mmol) in dry toluene (6 mL) was heated at 33° C. under a blanket of nitrogen overnight. Upon completion of the reaction, the toluene was removed and the compound purified via a flash chromatography (silica gel, 15% ethyl acetatelhexane) to give 6-(3-chloro-phenyl)-2,2,4,4-tetramethyl-1,4-dihydro-2H-benzo[d][1,3]oxazine (0.36 g, 68%) as a yellow oil. The oil was dissolved in ether at −78° C. and then treated with a solution of 1N HCl in ether to give the hydrochloride salt of the title compound as a yellow solid: $^1$H-NMR (DMSO-d$_6$) δ 7.70 (bs, 1H), 7.61 (d, 1H, J=7.82 Hz), 7.52 (bs, 1H), 7.44 (m, 2H), 7.33 (d, 1H, J=8.21 Hz), 6.87 (d, 1H, J=7.85 Hz), 1.5 (s, 6H), 1.4 (s, 6H); MS (ESI) m/z 302 ([M+H]$^+$, 100%); Anal. Calc. For C$_{18}$H$_{20}$ClNO: C, 63.91; H, 6.26; N, 4.14. Found: C, 64.08; H, 6.43; N, 4.14.

EXAMPLE 5

6-(3-Nitro-phenyl)-2,2,4,-trimethyl-1,4dihydro-2H-benzo[d][1,3]oxazine

Prepared from 1-(4-amino-3'-nitro-biphenyl-3-yl)-ethanol and acetone in the same fashion as that of Example 4. Yellow solid: mp 188–189° C.; Anal. Calc. For C$_{17}$H$_{18}$N$_2$O$_3$0.35 H$_2$O: C, 67.02; H, 6.19; N, 9.20. Found: C, 66.7; H, 5.89; N, 9.03.

EXAMPLE 6

4Amino-3'-chloro-biphenyl-3-carbonitrile

A mixture of 2-amino-5-bromobenzonitrile (10 g, 50 mmol), 3-chlorophenyl boronic acid (9.5 g, 60 mmol), tetrakis(triphenylphosphine)-palladium (0) (3.5 g, 3 mmol), and sodium carbonate (13 g, 120 mmol) in a mixture of DME and water (100 mL/25 mL) was degassed to remove the oxygen and then heated to 85° C. under a blanket of nitrogen for 5 hours. The reaction mixture was cooled to ambient temperature and quenched with a saturated aqueous ammonium chloride solution (80 mL). Ethyl acetate (200 mL) was added, the organic layer was separated, and the aqueous layer was extracted with ethyl acetate (3×40 mL). The combined organic layers were washed with brine and dried with MgSO$_4$. The solvent was removed in vacuo and the residue was purified by a silica gel flash chromatography (hexane:ethyl acetate/4:1) to afford 4-amino-3'-chloro-biphenyl-3-carbonitrile as an off-white solid (8 g, 87%): mp 118–119° C.; $^1$H-NMR (DMSO-d$_6$) δ 7.80 (d, 1H, J=2.3 Hz), 7.65–7.72 (m, 2H), 7.57 (d, 1H, J=8.0 Hz), 7.42 (t, 1H, J=7.9 Hz), 7.31 (m, 1H), 6.87 (d, 1H, J=8.7 Hz), 6.29 (br, 2H); Anal. Calc. For C$_{13}$H$_9$ClN$_2$: C, 68.28, H, 3.97, N, 12.25. Found: C, 67.68, H, 4.06, N, 11.89.

EXAMPLE 7

6(3-Chlorophenyl)-4-cyclopropyl-1H-guinazolin-2-one

Prepared using a similar procedure as described in the literature (Tucker et al. *J. Med. Chem.*, 1994, 37, 2437–2444). To a solution of cyclopropylmagnesium bromide prepared from magnesium (0.9 g, 37 mmol) and cyclopropyl bromide (3.2 mL, 40 mmol) in anhydrous THF was added at 50° C. under nitrogen a solution of 4-amino-3'-chloro-biphenyl-3-carbonitrile (2.3 g, 10 mmol) in anhydrous THF. After addition, the reaction mixture was kept at 50° C. for 30 minutes under nitrogen and treated with dimethyl carbonate in a dropwise manner. The reaction solution was stirred at 50° C. under nitrogen for 30 minutes and cooled to ambient temperature. A saturated aqueous ammonium chloride solution (30 mL) was added followed by addition of ethyl acetate (80 mL). The organic layer was separated and the aqueous layer was extracted with ethyl acetate (3×40 mL). The combined organic layers were washed with brine and dried with MgSO$_4$. After removal of the solvent, the residue was purified by a flash chromatography (silica gel, methylene chloride:methanol/25:1) to give 6-(3-chlorophenyl)-4-cyclopropyl-1H-quinazolin-2-one as ayellowish solid (0.55 g, 18%): mp 189–190° C.; $^1$H-NMR (DMSO-d$_6$) δ 11.71 (s, 1H, D$_2$O exchangeable), 8.56 (d, 1H, J=1.3 Hz), 8.09 (dd, 1H, J=8.6, 1.6 Hz), 7.92 (s, 1H), 7.77 (d, 1H, J=7.7 Hz), 7.52 (t, 1H, J=7.9 Hz), 7.45 (d, 1H, J=8.1 Hz), 7.36 (d, 1H, J=8.6 Hz), 3.15 (m, 1H), 1.20 (m, 4H); MS (CI) m/z 297 ([M+H]$^+$, 100%); Anal. Calc. For C$_{17}$H$_{13}$ClN$_2$O: C, 69.98, H, 4.49, N, 9.23. Found: C, 67.98, H, 4.46, N, 9.10.

EXAMPLE 8

6-(3Chlorophenyl)-4-cyclopropyl-1-(4-methoxybenzyl)-1H-quinazolin-2-one

To a suspension of 6-(3-chlorophenyl)-4-cyclopropyl-1H-quinazolin-2-one (0.5 g, 1.68 mmol) in anhydrous DMF was added potassium hexmethylsilyl amide (0.45 g, 2.1 mmol) at ambient temperature under nitrogen. The reaction mixture was stirred at ambient temperature for 30 minutes, treated with p-methoxy benzyl chloride (0.35 mL, 2.5 mmol), and heated at 55° C. for 5 hours. The mixture was then cooled to room temperature and quenched with a saturated aqueous ammoniun chloride solution (10 mL). Methylene chloride (50 mL) was added and organic layer was separated. The aqueous layer was extracted with methylene chloride (2×20 mL) and the combined organic layers were washed with brine and dried (MgSO$_4$). After removal of solvent, the residue was separated on a flash chromatography (silica gel, hexane:ethyl acetate/1:1) to afford 6-(3-chlorophenyl)-4-cyclopropyl-1-(4-methoxybenzyl)-1H-quinazolin-2-one as an off-white solid: mp 173–174° C.; $^1$H-NMR (DMSO-d$_6$) δ 8.65 (d, 1H, J=1.8 Hz), 8.10 (dd, 1H, J=8.9, 1.8 Hz), 7.93 (d, 1H, J=1.6 Hz), 7.79 (d, 1H, J=7.6 Hz), 7.53 (d, 2H, J=8.4 Hz), 7.46 (t, 1H, J=8.1 Hz), 7.21 (d, 2H, J=8.6 Hz), 6.88 (d, 2H, J=8.6 Hz), 5.41 (s, 2H), 3.73 (s, 3H), 3.18 (m, 1H), 1.18–1.27 (m, 4H); MS (CI) m/z 417([M+H]$^+$, 100%); Anal. Calc. For C$_{25}$H$_{21}$ClN$_2$O$_2$; C, 72.02, H, 5.08, N, 6.72. Found: C, 71.88, H, 4.91, N, 6.70.

6-(3-Chlorophenyl)-4-cyclopropyl-2-(4-methoxybenzyloxy)quinazoline was obtained as a side product, off-white solid: mp 158–159° C.; $^1$H-NMR (DMSO-d$_6$) δ 8.75 (d, 1H, J=1.7 Hz), 8.26 (dd, 1H, J=8.8, 1.8 Hz), 8.01 (s, 1H), 7.84 (m, 2H), 7.56 (t, 1H, J=7.9 Hz), 7.45 (m, 3H), 6.96 (d, 2H, J=8.6 Hz), 5.38 (s, 2H), 3.75 (s, 3H), 3.24 (m, 1H), 1.25 (m, 4H); MS (CI) m/z 417([M+H]$^+$, 100%); Anal. Calc. For $C_{25}H_{21}ClN_2O_2$: C, 72.02, H, 5.08, N, 6.72. Found: C, 72.19, H, 4.91, N, 6.65.

EXAMPLE 9

6-(3-Chlorophenyl)-4-cyclopropyl-4-methyl-3,4-dihydro-1H-quinazolin-2-one

To a solution of 6-(3-chlorophenyl)-4-cyclopropyl-1-(4-methoxybenzyl)-1H-quinazolin-2-one (0.25 g, 0.6 mmol) in anhydrous ether was added, at ambient temperature under nitrogen, magnesium triflate (0.78 g, 2.4 mmol). The mixture was stirred for 30 minutes and treated with a solution of methylmagnesium bromide in ether (3.0 M, 1.0 mL, 3.0 mmol). The reaction mixture was kept at room temperature under nitrogen for 3 hours and quenched with a mixture of a saturated aqueous ammonium chloride solution (10 mL) and 1N aqueous HCl solution (5 mL). The mixture was stirred at room temperature for 20 minutes and ethyl acetate (40 mL) was added. The organic layer was separated and the aqueous layer was extracted with ethyl acetate (3×10 mL). The combined organic layers were washed with brine and dried (MgSO$_4$). The solvent was removed and a half portion of the residue was dissolved in TFA (3 mL) and was stirred under nitrogen at room temperature for 72 hours. The solution was poured onto ice-water and the white precipitate obtained was collected on a filter. The solid was washed with water and then purified by a flash chromatography (methylene chloride:methanol/25:1, silica gel) to give 6-(3-chlorophenyl)-4-cyclopropyl-4-methyl-3,4-dihydro-1H-quinazolin-2-one as off-white solid(40 mg, 43%): mp 125–127° C.; $^1$H-NMR (DMSO-d$_6$) δ 9.21 (s, 1H), 7.71 (s, 1H), 7.61 (d, 1H, J=7.8 Hz), 7.55 (d, 1H, J=1.6 Hz), 7.47 (dd, 1H, J=8.3, 1.8 Hz), 7.45 (t, 1H, J=7.8 Hz), 7.36 (d, 1H, J=8.1 Hz), 6.84 (d, 1H, J=8.2 Hz), 6.79 (s, 1H), 1.54 (s, 3H), 1.11 (m, 1H), 0.42 (m, 1H), 0,15–0.20 (m, 3H); MS (ESI) m/z 313([M+H]$^+$, 100%).

EXAMPLE 10

6-(3-Chlorophenyl)-4-cyclopropyl-3,4-dimethyl3,4dihydro-1H-guinazolin-2-one

To a solution of half of the crude addition product from Example 9 in anhydrous DMF (5 mL) was added under nitrogen at room temperature sodium hydride (25 mg, 0.63 mmol). The mixture was stirred at ambient temperature for 30 minutes and treated with methyl iodide (0.5 mL, excess). After stirring for 3.5 hours, a mixture of saturated aqueous ammonium chloride and IN HCl aqueous solution (10 mL/5 mL) was added to the reaction mixture. Ethyl acetate (30 mL) was added and organic layer was separated. The aqueous layer was extracted with ethyl acetate (3×10 mL) and the combined organic layers were washed with brine and dried (MgSO$_4$). The solvent was removed and residue was dissolved in a mixture of methylene chloride and TFA (2 mL/2 mL). After stirring for 3 hours, the solution was poured onto ice-water and neutralized by addition of a saturated aqueous sodium bicarbonate solution. The ethyl acetate (30 mL) was added and the organic layer was separated. The aqueous layer was extracted with ethyl acetate (3×10 mL). The combined organic layers were washed with brine and dried (MgSO$_4$). The solvent was removed in vacuo and the residue was purified by a flash chromatography (silica gel, hexane:ethyl acetate/1:1) to afford 6-(3-chlorophenyl)-4-cyclopropyl-3,4-dimethyl-3,4-dihydro-1H-quinazolin-2-one as a white solid (11 mg, 11% for three steps): mp 193–194° C.; $^1$H-NMR (DMSO-d$_6$) δ 9.51 (s, 1H), 7.68 (s, 1H), 7.59 (d, 1H, J=8.0 Hz), 7.57 (d, 1H, J=1.6 Hz), 7.51 (dd, 1H, J=8.3, 1.7 Hz), 7.46 (t, 1H, J=7.8 Hz), 7.35 (d, 1H, J=8.1 Hz), 6.87 (d, 1H, J=8.3 Hz), 3.02 (s, 3H), 1.51 (s, 3H), 1.25 (m, 1H), 0.32–0.51 (m, 3H), 0.25 (m, 1H); MS (CI) m/z 327 ([M+H]$^+$, 100%). Anal. Calc. For $C_{19}H_{19}Cl_2O \cdot 0.3\ H_2O$: C, 68.69, H, 5.95, N, 8.43. Found: C, 68.69, H, 5.70, N, 8.18.

EXAMPLE 11

6-(3-Chlorophenyl)-4,4-dimethyl-3,4-dihydro-1H-quinolin-2-one

Sodium hydride (1.16 g, ca 29 mmol, 60% in oil) was washed with hexane (×3) then placed in anhydrous THF (50 mL) under nitrogen. To this slurry was then added dropwise a solution of 4-bromoaniline (5.0 g, 29 mmol) in dry THF (100 ml). After 0.5 h, the mixture was cooled to 0° C. and treated with a solution of 3,3-dimethylacryloyl chloride in anhydrous THF (30 ml). After 4 h, the mixture was quenched with saturated aqueous ammonium chloride solution, and extracted with diethyl ether. The organic layer was washed with water, brine, dried (Na$_2$SO$_4$) and evaporated. The residue was then crystallized from EtOAc/hexane to afford N-(3,3'-dimethylacryoloyl)-4-bromoaniline (3.36 g, 13.22 mmol, 46%) as a white solid: $^1$H NMR (CDCl$_3$) δ 7.42 (s, 4H), 7.06 (s, 1H), 5.68 (s, 1H), 2.21 (s, 3H), 1.09 (s, 3H); MS (EI) m/z 253 [M$^+$].

N-(3,3'-Dimethylacryoloyl)-4-bromoaniline (4.0 g, 15.38 mmol) was heated under nitrogen to ca. 130–140° C. causing the solid to melt. Aluminum chloride (3.07 g, 23 mmol) was added and heating continued. After 1 h, the mixture was cooled and quenched carefully with water and then extracted with dichloromethane (3×60 mL). The combined organic layers were washed with water, dried (MgSO$_4$) and evaporated. The residue was then subjected to column chromatography (SiO$_2$, EtOAc/hexane gradient elution) to afford 6-bromo-4,4-dimethyl-3,4-dihydro-1H-quinolin-2-one (1.69 g, 6.6 mmol, 47%) as a white solid: $^1$H-NMR (CDCl$_3$) δ 8.82 (s, 1H), 7.39 (d, 1H, J=2 Hz), 7.29 (dd, 1H, J=8.3, 2.0 Hz), 6.71 (d, 1H, J=8.0 Hz), 2.47 (s, 2H), 1.32 (s, 6H).

To a solution of the last cited compound (0.5 g, 1.96 mmol) in dimethoxyethane (15 mL) was added tetrakis (triphenylphosphine)palladium (0) (0.11 g, 0.09 mmol) under nitrogen. After 15 min., 3-chlorophenylboronic acid (0.6 g, 3.9 mmol) was added followed by potassium carbonate (1.62 g, 11.7 mmol) in water (7.5 mL). After 1.5 h at reflux, the mixture was cooled, filtered, and extracted with EtOAc. The organic layer was washed with water, dried (MgSO$_4$) and evaporated. The residue was then subjected to column chromatography (SiO$_2$, EtOAc:hexane/3:1) and crystallized from dichloromethane/hexane to afford 6-(3-chloro-phenyl)-4,4-dimethyl-3,4-dihydro-1H-quinolin-2-one (0.21 g, 0.73 mmol, 37%) as a white solid; mp. 211–215° C.; $^1$H-NMR (CDCl$_3$) δ 8.48 (s, 1H), 7.53 (s, 1H), 7.47 (d, 1H, J=2.0 Hz), 7.44–7.29 (m, 4H), 6.87 (1H, d, J=2.0 Hz), 2.54 (s, 2H), 1.39 (s, 6H); MS ((−)ES) m/z 284 [M−H]$^−$.

EXAMPLE 12

Pharmacology

The compounds of this invention were tested in the relevant assay as described below and their potency are in the range of 0.01 nM to 5 μM in the in vitro assays and 0.001 to 300 mg/kg in the in vivo assays. The selected examples are listed below

TABLE 1

| Compound | $R_1$ | $R_2$ | $R_3$ | hPR CV-1 $IC_{50}$ (nM) |
|---|---|---|---|---|
| 1 | Me | Me | Cl | 10.0 |
| 2 | $CF_3$ | Me | Cl | 50.0 |
| 3 | Me | H | $NO_2$ | 1675 |

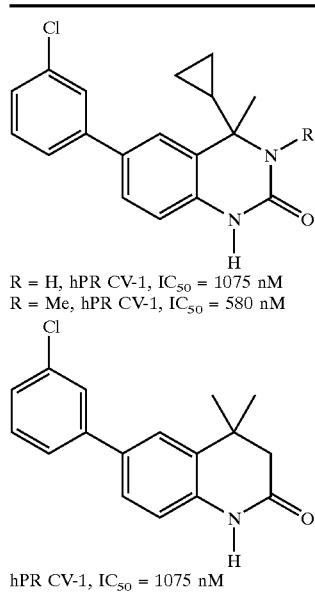

R = H, hPR CV-1, $IC_{50}$ = 1075 nM
R = Me, hPR CV-1, $IC_{50}$ = 580 nM hPR CV-1, $IC_{50}$ = 1075 nM

A. In-vitro Biology

The in-vitro biology is determined by (1) competitive Radioligand Binding: using the A-form of the human progesterone receptor with progesterone as the radioligand; (2) co-transfection assay, which provides functional activity expressed as agonist EC50 and Antagonist IC50 values; (3) a T47D cell proliferation, which is a further functional assay which also provides agonist and antagonist data; and (4) T47D cell alkaline phosphatase assay, which is a further functional assay which also provides agonist and antagonist data.

1. hPR Binding Assay

This assay is carried out in accordance with: Pathirana, C.; Stein, R. B.; Berger, T. S.; Fenical, W.; Ianiro, T.; Mais, D. E.; Torres, A.; Glodman, M. E., Nonsteroidal human progesterone receptor modulators from the marine alga cymoplia barbata, J. Steroid Biochem. Mol. Biol., 1992, 41, 733–738.

2. PRE-luciferase Assay in CV-1 Cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium:

The growth medium was as follows: DMEM (BioWhittaker) containing 10% (v/v) fetal bovine serum (heat inactivated), 0.1 mM MEM non-essential amino acids, 100 U/ml penicillin, 100 mg/ml streptormycin, and 2 mM GlutaMax (GIBCO, BRL). The experimental medium was as follows: DMEM (Bio Whittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment, and Luciferase Assay

Stock CV-1 cells are maintained in growth medium. Co-transfection is done using $1.2 \times 10^7$ cells, 5 mg pLEM plasmid with hPR-B inserted at Sph1 and BamH1 sites, 10 mg pGL3 plasrmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental mediutm Cells are then treated with reference or test compounds in experimental medium Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Pronmega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results:

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds:

Progesterone and trimegestone are reference progestins and RU486 is the reference antiprogestin. All reference compounds are run in full dose-response curves and the $EC_{50}$ or $IC_{50}$ values are calculated.

TABLE 2

Estimated $EC_{50}$, standard error (SE), and 95% confidence intervals (CI) for reference progestins from three individual studies

| Compound | Exp. | EC50 (nM) | SE | 95% CI lower | 95% CI upper |
|---|---|---|---|---|---|
| Progesterone | 1 | 0.616 | 0.026 | 0.509 | 0.746 |
| | 2 | 0.402 | 0.019 | 0.323 | 0.501 |
| | 3 | 0.486 | 0.028 | 0.371 | 0.637 |
| Trimegestone | 1 | 0.0075 | 0.0002 | 0.0066 | 0.0085 |
| | 2 | 0.0081 | 0.0003 | 0.0070 | 0.0094 |
| | 3 | 0.0067 | 0.0003 | 0.0055 | 0.0082 |

TABLE 3

Estimated IC$_{50}$, standard error (SE), and 95% confident interval (CI) for the antiprogestin, RU486 from three individual studies

| Compound | Exp. | EC50 (nM) | SE | 95% CI lower | upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestatinal activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05).

EC$_{50}$: Concentration of a compound that gives half-maxi increase PRE-luciferase activity (default-nM) with SE.

IC$_{50}$: Concentration of a compound that gives half-maximal decrease in 3 nM progesterone induced PRE-luciferase activity (default-nM) with SE.

3. T47D Cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium:

DMEM:F12 (1:1) (GIBCO, BRL) supplemented with 10% (v/v) fetal bovine serum (not heat-inactivated), 10 U/ml penicillin, 100 mg/ml streptornycin, and 2 mM GlutaMax (GIBCO, BRL).

b. Treatment Medium:

Minimum Essential Medium (MEM) (#51200-038GIBCO, BRL) phenol red-free supplemented with 0.5% charcoal stripped fetal bovine serum, 100 U/ml penicillin, 200 mg/ml streptornycin, and 2 mM GlutaMax (GIBCO, BRL).

c. Cell Culture

Stock T47 D cells are maintained in growth medium. For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10–20 min depending upon the potency of tested compounds. Then 25 µl of 1 M sulfuric acid is added to each well to stop color reaction and optical density is read in a plate reader at 450 nm within 5 min.

e. Analysis of Results:

Square root-transformed data are used for analysis of variance and nonlinear dose response curve fitting for both agonist and antagonist modes. Huber weighting is used to downweight the effects of outliers. EC$_{50}$ or IC$_{50}$ values are calculated from the retransformed values. JMP software (SAS Institute, Inc.) is used for both one-way analysis of variance and non-linear dose response analyses in both single dose and dose response studies.

f. Reference Compounds:

Trimegestone and medroxyprogesterone acetate (MPA) are reference progestins and RU486 is the reference antiprogestin. All reference compounds are run in full dose-response curves and the EC$_{50}$ or IC$_{50}$ values are calculated.

TABLE 4

Estimated EC$_{50}$, standard error (SE), and 95% confidence intervals (CI) for individual studies

| Compound | Exp | EC$_{50}$ (nM) | SE | 95% CI lower | upper |
|---|---|---|---|---|---|
| Trimegestone | 1 | 0.017 | 0.003 | 0.007 | 0.040 |
|  | 2 | 0.014 | 0.001 | 0.011 | 0.017 |
|  | 3 | 0.019 | 0.001 | 0.016 | 0.024 |
| MPA | 1 | 0.019 | 0.001 | 0.013 | 0.027 |
|  | 2 | 0.017 | 0.001 | 0.011 | 0.024 |

TABLE 5

Estimated IC$_{50}$, standard error, and 95% cinfident interval for the antiprogestin, RU486

| Compound | Exp | IC$_{50}$ (nM) | SE | 95% CI lower | upper |
|---|---|---|---|---|---|
| RU486 | 1 | 0.011 | 0.001 | 0.008 | 0.014 |
|  | 2 | 0.016 | 0.001 | 0.014 | 0.020 |
|  | 3 | 0.018 | 0.001 | 0.014 | 0.022 |

EC$_{50}$: Concentration of a compound that gives half-maximal increase in BrdU incorporation with SE; IC$_{50}$: Concentration of a compound that gives half-maximal decrease in 0.1 trimegestone induced BrdU incorporation with SE.

4. T47D Cell Alkaline Phosphatase Assay

The purpose of this assay is to identify progestins or antiprogestins by determining a compound's effect on alkaline phosphatase activity in T47D cells. The materials and methods used in this assay are as follows.

a. Culture Medium:

DMEM:F12 (1:1) (GIBCO, BRL) supplemented with 5% (v/v) charcoal stripped fetal bovine serum (not heat-inactivated), 100 U/ml penicillin, 100 µg/ml streptonycin, and 2 mM GlutaMax (GIBCO, BRL).

b. Alkaline Phosphatase Assay Buffer:

I. 0.1 M Tris-HCl, pH 9.8, containing 0.2% Triton X-100

II. 0.1 M Tris-HCl, pH 9.8 containing 4 mM p-nitrophenyl phosphate (Sigma).

c. Cell Culture and Treatment:

Frozen T47D cells were thawed in a 37° C. water bath and diluted to 280,000 cells/ml in culture medium. To each well in a 96-well plate (Falcon, Becton Dickinson Labware), 180

µl of diluted cell suspension was added. Twenty µl of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hr.

d. Alkaline Phosphatase Enzyme Assay:

At the end of treatment, the medium was removed from the plate and fifty µl of assay buffer I was added to each well. The plates were shaken in a titer plate shaker for 15 min. Then 150 µl of assay buffer II was added to each well. Optical density measurements were taken at 5 min intervals for 30 min at a test wavelength of 405 nM.

e. Analysis of Results: Analysis of Dose-response Data

For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds:

Progesterone and trimegestone are reference progestins and RU486 is the reference antiprogestin. All reference compounds are run in fill dose response curves and the $EC_{50}$ or $IC_{50}$ values are calculated.

TABLE 6

Estimated $EC_{50}$, standard error (SE), and 95% confidence intervals (CI) for reference progestins from three independent experiments

| Compound | Exp | $EC_{50}$ (nM) | SE | 95% CI lower | 95% CI upper |
|---|---|---|---|---|---|
| Progesterone | 1 | 0.839 | 0.030 | 0.706 | 0.996 |
|  | 2 | 0.639 | 0.006 | 0.611 | 0.669 |
|  | 3 | 1.286 | 0.029 | 1.158 | 1.429 |
| Trimegestone | 1 | 0.084 | 0.002 | 0.076 | 0.091 |
|  | 2 | 0.076 | 0.001 | 0.072 | 0.080 |
|  | 3 | 0.160 | 0.004 | 0.141 | 0.181 |

TABLE 7

Estimated $IC_{50}$, standard error (SE), and 95% confident interval for the reference antiprogestin RU486 from three independent experiments

| Compound | Exp | $IC_{50}$ (nM) | SE | 95% CI lower | 95% CI upper |
|---|---|---|---|---|---|
| RU486 | 1 | 0.103 | 0.002 | 0.092 | 0.115 |
|  | 2 | 0.120 | 0.001 | 0.115 | 0.126 |
|  | 3 | 0.094 | 0.007 | 0.066 | 0.134 |

B. In-vivo Biology

The primary in-vivo assay is the rat decidualization model which may be used to determine progestational effects of both agonists and antagonists. The secondary in-vivo assay is the rat ovulation inhibition model which is under development and hence the protocol is un-available.

1. Rat decidualization assay

The objective of this procedure is used to evaluate the effect of progestins and antiprogestins on rat uterine decidualization and compare the relative potencies of various test compounds. The materials and methods used in this assay are as follows.

a. Methods:

Test compounds are dissolved in 100% ethanol and mixed with corn oil (vehicle). Stock solutions of the test compounds in oil (Mazola™) are then prepared by heating (~80° C.) the mixture to evaporate ethanol.

Test compounds are subsequently diluted with 100% corn oil or 10% ethanol in corn oil prior to the treatment of animals. No difference in decidual response was found when these two vehicles were compared.

b. Animals (RACUC protocol #5002)

Ovariectorrized mature female Sprague-Dawley rats (~60-day old and 230 g) are obtained from Taconic (Taconic Farms, NY) following surgery. Ovariectony is performed at least 10 days prior to treatment to reduce circulating sex steroids. Animals are housed under 12 hr light/dark cycle and given standard rat chow and water ad libitum.

c. Treatment

Rats are weighed and randomly assigned to groups of 4 or 5 before treatment. Test compounds in 0.2 ml vehicle are administered by subcutaneous injection in the nape of the neck or by lavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing

Doses are prepared based upon mg/kg mean group body weight. In all studies, a control group receiving vehicle is included. Determination of dose-response curves is carried out using doses with half log increases (e.g. 0.1, 0.3, 1.0, 3.0 mg/kg . . . ).

e. Decidual Induction

Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $CO_2$ asphyxiation and body weight measured. Uteri are removed and trimmed of fat. Decidualized (D-horn) and control (C-horn) uterine horns are weighed separately.

f. Analysis of Results:

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds:

All progestin reference compounds were run in full dose-response curves and the $EC_{50}$ for uterine wet weight were calculated.

TABLE 8

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
|  | 2 | 6.21 | 1.12 | 4.41 | 8.76 |

TABLE 8-continued

Estimated EC$_{50}$, standard error (SE), and 95% confidence intervals for individual studies

| Compound | Exp | EC$_{50}$ (mg/kg, s.c.) | SE | 95% CI lower | 95% CI upper |
|---|---|---|---|---|---|
| 3-Ketodesogestrel | 1 | 0.11 | 0.02 | 0.07 | 0.16 |
| | 2 | 0.10 | 0.05 | 0.11 | 0.25 |
| | 3 | 0.06 | 0.03 | 0.03 | 0.14 |
| Levonorgestrel | 1 | 0.08 | 0.03 | 0.04 | 0.16 |
| | 2 | 0.12 | 0.02 | 0.09 | 0.17 |
| | 3 | 0.09 | 0.02 | 0.06 | 0.13 |
| | 4 | 0.09 | 0.02 | 0.06 | 0.14 |
| MPA | 1 | 0.42 | 0.03 | 0.29 | 0.60 |
| | 2 | 0.39 | 0.03 | 0.29 | 0.60 |
| | 3 | 0.39 | 0.04 | 0.25 | 0.61 |

TABLE 9

Estimated average EC$_{50}$, standard error, and 95% confidence intervals for dose-response curves of 3 reference compounds

| Compound | EC50 (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 10

Estimated IC$_{50}$, standard error, and 95% confident interval for the antiprogestin, RU 486

| Compound | Exp. | IC$_{50}$ (mg/kg, s.c.) | SE | 95% CI lower | 95% CI upper |
|---|---|---|---|---|---|
| RU 486 | 1 | 0.21 | 0.07 | 0.05 | 0.96 |
| | 2 | 0.14 | 0.02 | 0.08 | 0.27 |

Concentration: Compound concentration in assay (default-mg/kg body weight)
Route of administration: Route the compound is administered to the animals
Body weight: Mean total animal body weight (default-kg)
D-horn: Wet weight of decidualized uterine horn (default-mg)
C-horn: Wet weight of control uterine horn (default-mg)
Decidual response: [(D-C)/C]×100%
Progestational activity: Compounds that induce decidualization significantly (p<0.05) compared to vehicle control are considered active
Antiprogestational activity: Compounds that decrease EC$_{50}$ progesterone induced decidualization significantly (p<0.05)
EC$_5$0 for uterine weight: Concentration of compound that gives half-maximal increase in decidual response (default-mg/kg)
IC$_{50}$ for uterine weight: Concentration of compound that gives half-maximal decrease in EC$_{50}$ progesterone induced decidual response (default-mg/kg)

EXAMPLE 13

5-(2,4,4-Trimethyl-1,4-dihydro-2H-3,1-benzoxazin-6-yl)thiophene-2-carbonitrile

A solution of 2-amino-5-bromobenzoic acid (10 g, 46 mmol) in dry THF (200 mL) was treated at −78° C. under nitrogen with a solution of methylmagnesium brormide in ether (3.0 M, 90 mL, 270 mmol). The reaction mixture was slowly warmed to ambient temperature, kept stirring for 48 hours under nitrogen and then poured into a cold 0.5 N aqueous hydrochloride solution (300 mL). The mixture was neutralized with aqueous 1 N sodium hydroxide solution and ethyl acetate (300 mL) was added. The organic layer was separated and aqueous layer was extracted with ethyl acetate (3×100 mL). The combined organic layers were washed with brine and dried (MgSO$_4$). After removal of solvent in vacuo, the residue was purified by a silica gel flash column chromatography(hexane:ethyl acetate/3:2) to give 2-(2-amino-5-bromophenyl)propan-2-ol as off-white solid (6 g, 57%): mp 62–63° C.; $^1$H-NMR (CDCl$_3$) δ 7.19 (d, 1H, J=2.3 Hz), 7.12 (dd, 1H, J=8.4, 2.3 Hz), 6.51 (d, 1H, J=8.4 Hz), 4.70 (s, 2H), 1.82 (s, 1H), 1.65 (s, 6H).

To a solution of 2-(2-amino-5-bromophenyl)propan-2-ol (27 g, 125 mmol) in anhydrous toluene was added at ambient temperature under a blanket of nitrogen acetylaldehyde (10.5 mL, 187 mmol). After 10 minutes, the mixture was passed through a pad of silica gel and filtrate was concentrated to yield 6-bromo-2,4,4-trimethyl-1,4-dihydro-2H-3,1-benzoxazine as off-white solid (25 g, 78%): $^1$H-NMR (DMSO-d$_6$) δ 7.22 (d, 1H, J=2.2 Hz), 7.08 (dd, 1H, J=8.6, 2.3 Hz), 6.51 (d, 1H, J=8.6 Hz), 6.36 (s, 1H), 4.72 (m, 1H), 1.45 (s, 3H), 1.40 (s, 3H), 1.25 (d, 3H, J=5.5 Hz).

A mixture of 6-bromo-2,4,4-trimethyl-1,4-dihydro-2H-3,1-benzoxazine (3.6 g, 14 mmol), bis(pinacolato)diboron (5 g, 19.7 mmol), potassium acetate (4 g, 41 mmol), and [1,1'-bis(diphenylphosphino)ferrocene]palladium (II) chloride (1:1 complex with methylene chloride, 0.4 g, 0.5 mmol) in DMF (80 ml,) was subject to a positive nitrogen flow to remove oxygen and then heated at 85° C. under a blanket of nitrogen for 18 hours. The reaction mixture was allowed to cool to ambient temperature, treated with 5-bromo-2-thiophenecarbonitrile (4 g, 21 mmol), [1,1'-bis(diphenylphosphino)ferrocene]palladium (II) chloride (1:1 complex with methylene chloride, 0.4 g, 0.5 mmol), and aqueous sodium carbonate solution (2M, 35 mL, 70 mmol), and then heated at 85° C. under nitrogen for 3 hours. The reaction mixture was allowed to cool to ambient temperature, brine (100 mL) and ethyl acetate (150 mL) were added. The organic layer was separated and aqueous layer was extracted with ethyl acetate (3×50 mL). The combined organic layers were dried (MgSO$_4$) and concentrated. The residue was purified by a flash silica gel column chromatography(THF:hexane/1:4) to afford the title compound as an off-white solid (1 g, 25%): mp 172–173° C.; $^1$H-NMR (DMSO-d$_6$) δ 7.88 (d, 1H, J=4.0 Hz), 7.47 (d, 1H, J=4.0 Hz), 7.43 (d, 1H, J=2.0 Hz), 7.32 (dd, 1H, J=8.36, 2.4 Hz), 6.77 (s, 1H), 6.60 (d, 1H, J=8.4 Hz), 4.83 (m, 1H), 1.51 (s, 3H), 1.48 (s, 3H), 1.28 (d, 3H, J=5.6 Hz); MS (ESI) m/z 283 [M−H]$^-$.

EXAMPLE 14

3-Fluoro-5-(2,4,4-trimethyl-1,4-dihydro-2H-3,1-benzoxazin-6-yl)benzonitrile

Prepared according to the procedure for Example 13 from 6-bromo-2,4,4-trimethyl-1,4-dihydro-2H-3,1-benzoxazine and 3-bomo-5-fluorobenzonitrile. A white solid: mp 163–164° C.; $^1$H-NMR (DMSO-d$_6$) δ 8.02 (t, 1H, J=1.5 Hz), 7.87 (dt, 1H, J=10.6, 2.2 Hz), 7.65 (m, 1H), 7.55 (d, 1H, J=2.2 Hz), 7.44 (dd, 1H, J=8.4, 2.2 Hz), 6.63 (d, 1H, J=8.4 Hz), 6.58 (s, 1H), 4.82 (m, 1H), 1.52 (s, 3H), 1.50 (s, 3H), 1.28 (d, 3H, J=5.1 Hz), MS (ESI) m/z 295 [M−H]$^-$.

EXAMPLE 15

4-(2,4,4-Trimethyl-1,4-dihydro-2H-3,1-benzoxazin-6-yl)thiophene-2-carbonitrile

Prepared according to the procedure for Example 13 from 6-bromo-2,4,4-trimethyl-1,4-dihydro-2H-3,1-benzoxazine and 4-bromo-2-thiophenecarbonitrile. An off-white solid: mp 175–176° C.; $^1$H-NMR (DMSO-d$_6$) δ 8.39 (d, 1H, J=1.5 Hz), 8.13 (d, 1H, J=1.5 Hz), 7.47 (d, 1H, J=1.9 Hz), 7.36 (dd, 1H, J=8.4, 1.9 Hz), 6.59 (d, 1H, J=8.4 Hz), 6.41 (s, 1H), 4.78 (m, 1H), 1.51 (s, 3H), 1.47 (s, 3H), 1.28 (d, 3H, J=5.4 Hz); MS (ESI) m/z 285 [M+H]$^+$.

EXAMPLE 16

4-Methyl-5(2,4,4-trimethyl-1,4-dihydro-2H-3,1-benzoxazin-6-yl)thiophene-2-carboxnitrile Prepared according to the procedure for Example 13 from 6-bromo-2,4,4-trimethyl-1,4-dihydro-2H-3,1-benzoxazine and 5-bromo-4-methyl-2-thiophenecarbonitrile. A yellowish solid: mp 145–146° C.; $^1$H-NMR (DMSO-d$_6$) δ 7.79 (s, 1H), 7.18 (d, 1H, J=2.0 Hz), 7.13 (dd, 1H, J=8.4, 2.0 Hz), 6.68 (s, 1H), 6.54 (d, 1H, J=8.3 Hz), 4.83 (m, 1H), 2.26 (s, 3H), 1.49 (s, 3H), 1.46 (s, 3H), 1. 28 (d, 3H, J=5.5 Hz); MS (ESI) m/z 299 [M+H]$^+$.

EXAMPLE 17

3-[(2R,4S)-2,4-Dimethyl-4-phenyl-1,4-dihydro-2H-3,1-benzoxazin-6-yl]-5-fluorobenzonitrile To a solution of 2-amino-4-bromobenzonitrile (5 g, 25 mmol) in anhydrous THF, was added at 0° C. under nitrogen, phenylmagnesium bromide (3 M in ether, 25 mL, 75 mmol). The mixture was allowed to warm to room temperature, stirred under nitrogen for 15 hours, and treated with 2N aqueous hydrogen chloride solution (100 mL). The aqueous solution was heated to 50° C. for 3 hours, cooled to room temperature, and neutralized with a cold saturated sodium bicarbonate solution. Ethyl acetate (100 mL) was added and the organic layer was separated and aqueous layer was extracted with ethyl acetate (3×40 mL). The combined organic layers were dried (MgSO$_4$) and evaporated. The residue was purified by a flash column chromatography (silica gel, hexane:ethyl acetate/4:1) to yield (2-amino-5-bromophenyl)(phenyl)methanone as a yellow crystal (2.13 g, 31%): MS (ESI) m/z 276/278 (M+H)$^+$.

To a solution of (2-amino-5-bromophenyl)(phenyl) methanone (1 g, 3.6 mmol) in anhydrous THF (15 mL) was added at room temperature under nitrogen methylmagnesium bromide (3M in ether, 3 mL, 9 mmol). After 3 hours, the mixture was treated with a saturated aqueous ammonium sulfate solution (30 mL) and ethyl acetate (50 mL). The organic layer was separated, dried (MgSO$_4$), and evaporated. The residue was then dissolved in anhydrous toluene and treated at ambient temperature under nitrogen with acetylaldehyde (2 mL). After 2 minutes, the solvent was removed and residue was purified by a column chromatography(silica gel, hexane:ethyl acetate/4:1) to afford 6-bromo-2,4-dimethyl-4-phenyl-1,4-dihydro-2H-3,1-benzoxazine as a yellowish solid (0.8 g, 70%): MS (ESI) m/z 318/320 [M+H]$^+$.

A mixture of 6-bromo-2,4-dimethyl-4-phenyl-1,4-dihydro-2H-3,1-benzoxazine (0.6 g, 1.9 mmol), 3-cyano-5-fluorobenzene boronic acid (0.45 g, 2.7 mmol), tetrakis (triphenylphosphine)palladium (0) (0.2 g, 0.17 mmol), sodium carbonate (0.6 g, 5.7 mmol) in a mixture of DME and water (20/5 mL) was subject to a positive nitrogen flow to remove oxygen and then heated to 85° C. under a blanket of nitrogen for 2 hours. The mixture was allowed to cool to ambient temperature. Brine (30 mL) and ethyl acetate (100 mL) were added. The organic layer was separated and aqueous layer was extracted with ethyl acetate (3×30 mL). The combined organic layers were dried (MgSO$_4$), and evaporated. The residue was purified by a silica gel column chromatography(hexane:ethyl acetate/4:1) to afford the title compound as off-white solid (0.09 g, 13%): mp128–129° C.; $^1$H-NMR (DMSO-d$_6$) δ 8.08 (s, 1H), 7.91 (dt, 1H, J=10.7, 1.9 Hz), 7.71 (d, 1H, J=2.0 Hz), 7.65 (m, 1H), 7.57 (dd, 1H, J=8.8, 2.4 Hz), 7.32–7.36 (m, 2H), 7.24–7.29 (m, 3H), 6.71 (d, 1H, J=1.6 Hz), 6.69 (d, 1H, J=8.3 Hz), 4.33 (m, 1H), 1.84 (s, 3H), 1.24 (d, 3H, J=5.5 Hz); MS (ESI) m/z 357 [M–H]$^-$.

EXAMPLE 18 tert-Butyl 2-cyano-5-(2,4,4-trimethyl-1,4-dihydro-2H-3,1-benzoxazin-6-yl)-1H-pyrrole-1-carboxlate tert-Butyl-5-(2,4,4-trimethyl-1,4-dihydro-2H-3,1-benzoxazin-6-yl)-1 H-pyrrole-1-carboxylate was prepared according to the coupling procedure for Example 17 from 6-bromo-2,4,4-trimethyl-1,4-dihydro-2H-3,1-benzoxazine and 1-t-butoxycarbonylpyrrol-2-yl boronic acid. To a solution of tert-butyl-5-(2,4,4-trimethyl-1,4-dihydro-2H-3,1-benzoxazim-6-yl)-1H-pyrrole-l-carboxylate (1 g, 2.9 mmol) in anhydrous THF (20 mL) was added at –78° C. under nitrogen chlorosulfonyl isocyanate (0.35 mL, 4.0 mmol). The mixture was kept stirring at –78° C. under nitrogen for 2 hours, treated with anhydrous DMF (5 mL), and allowed to warm to room temperature. Aqueous ammonium sulfate solution (50 mL) and ethyl acetate (100 mL) was added and organic layer was separated, dried (MgSO$_4$), and evaporated. The residue was purified by a silica gel column chromatography(hexane:ethyl acetate/4:1) to afford the title compound as a white solid (0.019 g, 1.78%): $^1$H-NMR (DMSO-d$_6$) δ 7.48 (d, 1H, J=2.0 Hz), 7.36 (dd, 1H, J=8.3, 2.0 Hz), 7.32 (d, 1H, J=3.6 Hz), 7.14 (d, 1H, J=8.3 Hz), 6.46 (d, 1H, J=4.0 Hz), 5.35 (q, 1H, J=5.2 Hz), 1.58 (d, 3H, J=5.6 Hz), 1.56 (s, 3H), 1.51 (s, 3H), 1.38 (s, 9H); MS (ESI) m/z 366 [M--H]$^-$.

EXAMPLE 19

9H-Fluoren-9-ylmethyl-6-[1-(tert-butoxycarbonyl)-5-cyano-1H-pyrrol-2-yl]-2,4,4-trimethyl-2H-3,1-benzoxazine-1(4H)-carboxylate A mixture of tert-butyl-5-(2,4,4-trimethyl-1,4-dihydro-2H-3,1-benzoxazin-6-yl)-1H-pyrrole-1-carboxylate (1.7 g, 4.96 mmol), 9-fluorenylmethyl chloroformate (1.92 g, 7.5 mL), sodium carbonate (4 g, 37 mmol) in dioxane (50 mL) and water (50 mL) was stirred at room temperature under a blanket of nitrogen for 6 hours. Ethyl acetate (100 mL) was added and organic layer was separated, dried (MgSO$_4$), and evaporated. The residue was purified by a silica gel column chromatography(hexane:ethyl acetate/6:1) to afford 9H-fluoren-9-ylmethyl-6-[1-(tert-butoxycarbonyl)-1H-pyrrol-2-yl]-2,4,4-trimethyl-2H-3,1-benzoxazine-1(4H)-carboxylate as a clean oil.

Using the procedure for Example 18, the title compound (0.8 g, 65%) was prepared from 9H-fluoren-9-ylmethyl-6-[1-(tert-butoxycarbonyl)-1H-pyrrol-2-yl]-2,4,4-trimethyl-2H-3,1-benzoxazine-1(4H)carboxylate (1.2 g, 2.1 mmol) and chlorosulfonyl isocyanate (0.28 mL, 3.1 mmol). A white solid: mp 135–136° C.; $^1$H-NMR (DMSO-d$_6$) δ 7.90 (t, 2H, J=6.7 Hz), 7.64 (d, 1H, J=7.5 Hz), 7.59 (d, 1H, J=7.1 Hz), 7.40 (td, 2H, J=7.2, 2.0 Hz), 7.31–7.34 (m, 3H), 7.29 (d, 1H, J=1.2 Hz), 7.04–7.09 (m, 2H), 6.44 (d, 1H, J=3.57 Hz), 5.30 (q, 1H, J=5.6 Hz), 4.86 (dd, 1H, J=10.7, 5.2 Hz), 4.64 (dd, 1H, J=10.8, 5.2 Hz), 4.33 (t, 1H, J=4.7 Hz). 1.50 (s, 3H), 1.30 (s, 9H), 1.20 (s, 3H), 1.03 (d, 3H, J=5.6 Hz); MS (ESI) m/z 590 [M+H]$^+$.

EXAMPLE 20

5-(2,4,4-Trimethyl-1,4-dihydro-2H-3,1-benzoxazin-6-yl)1H-pyrrole-2-carbonitrile 9H-Fluoren-9-ylmethyl-6-[1-(tert-butoxycarbonyl)-5-cyano-1H-pyrrol-2-yl]-2,4,4-trimethyl-2H-3,1-benzoxazine-1(4H)-carboxylate (0.5 g, 0.84 nimol) was heated under a blanket of nitrogen at 160° C. until gas evolution ceased. After cooling to room temperature, 9H-fluoren-9-ylmethyl-6-[5-cyano-1H-pyrrol-2-yl]-2,4,4-trimethyl-2H-3,1-benzoxazine-1(4H)-carboxylate was obtained as a white solid (0.4 g, 97%).

A solution of 9H-fluoren-9-ylmethyl-6-[5-cyano-1H-pyrrol-2-yl]-2,4,4-trimethyl-2H-3,1-benzoxazine-1(4H)-carboxylate (0.1 g, 0.2 mmol) in 20% piperidine in DMF (5 mL) was stirred at room temperature under nitrogen for 10 minutes. The mixture was poured into a saturated ammonium sulfate solution (30 mL) and extracted with diethyl ether (3×30 mL). The combined organic layers were dried (MgSO$_4$) and evaporated. The residue was purified by a silica gel column chromatography(hexane: ethyl acetate/3:1) to afford the title compound as a white solid (0.03 g, 56%): mp 201–202° C., $^1$H-NMR (DMSO-d$_6$) δ 12.27 (s, 1H), 7.44 (d, 1H, J=2.1 Hz), 7.32 (dd, 1H, J=8.3, 1.1 Hz), 6.92 (dd, 1H, J=4.1, 2.6 Hz), 6.57 (d, 1H, J=8.3 Hz), 6.50 (dd, 1H, J=4.2, 2.6 Hz), 6.40 (s, 1H), 4.77–4.80 (m, 1H), 1.51 (s, 3H), 1.46 (s, 3H), 1.27 (d, 3H, J=5.7 Hz); MS (ESI) m/z 266 [M−H]$^-$.

EXAMPLE 21

9H-Fluoren-9-ylmethyl 6-(5cyano-1-methyl-1H-pyrrol-2-yl)-2,4,4-trimethyl-2H-'3,1-benzoxazine-1(4H)-carboxylate A mixture of 9H-fluoren-9-ylethyl-6-[5-cyano-1H-pyrrol-2-yl]-2,4,4-trimethyl-2H-3,1-benzoxazine-1(4H)-carboxylate (0.4 g, 0.8 mmol) and potassium carbonate (1.5 g) in anhydrous DMF was treated at ambient temperature under a blanket of nitrogen with iodomethane (1.5 mL, excess). The mixture was stirred for 30 minutes. A saturated ammonium sulfate solution (50 mL) and ethyl acetate (50 mL) was added. The organic layer was separated and aqueous layer was extracted with ethyl acetate (3×5 mL). The combined organic layers were dried (MgSO$_4$), evaporated to yield the title compound as a white solid (0.35 g, 87%): mp 63–64° C.; $^1$H-NMR (DMSO-d$_6$) δ 7.90 (m, 2H), 7.62 (d, 1H, J=7.7 Hz), 7.58 (d, 1H, J=7.7 Hz), 7.40 (m, 2H), 7.29–7.32 (m, 3H), 7.14 (dd, 1H, J=8.1, 1.9 Hz), 7.01–7.04 (m, 2H), 6.33 (d, 1H, J=4.3Hz), 5.31 (q, 1H, J=5.8 Hz), 4.88 (dd, 1H, J=10.8, 5.0 Hz), 4.65 (dd, 1H, J=10.8, 4.6 Hz), 4.34 (t, 1H, J=4.6 Hz), 3.71 (s, 3H), 1.52 (s, 3H), 1.21 (s, 3H), 1.06 (d, 3H, J=5.4 Hz); MS (ESI) m/z 504 [M+H]$^+$.

EXAMPLE 22

1-Methyl-S(2,4,4-trimethyl-1,4-dihydro-2H-3,1-benzoxazin-6-yl)-1H-pyrrole-2-carbonitrile Prepared according to the procedure for Example 20 from 9H-fluoren-9-ylmethyl 6-(5-cyano-1-methyl-1H-pyrrol-2-yl)-2,4,4-trimethyl-2H-'3,1-benzoxazine-1(4H)-carboxylate (0.3 g, 0.6 mmol) and 20% piperidine in DMF. A white solid (0.07 g, 42%): mp 195–196° C.; $^1$H-NMR (DMSO-d$_6$) δ 7.16 (d, 1H, J=2.8 Hz), 7.08 (dd, 1H,J=8.1, 1.9 Hz), 6.98 (d, 1H, J=4.1 Hz), 6.63 (d, 1H, J=8.5 Hz), 6.61 (s, 1H), 6.20 (d, 1H, J=4.1 Hz), 4.79–4.81 (m, 1H), 3.67 (s, 3H), 1.49 (s, 3H), 1.45 (s, 3H), 1.27 (d, 3H, J=5.5 Hz); MS (ESI) m/z 282 [M+H]$^+$.

EXAMPLE 23

5(2-Methylspiro[4H-3,1-benzoxazine-4,1'-cyclopentane]-6-yl)-4 methyl-2-thiophenecarbonitrile 2-Methyl-6-bromospiro[4H-3,1-benzoxazine-4,1'-cyclopentane] was prepared using the same procedure as for 6-bromo-2,4,4-trimethyl-1,4-dihydro-2H-3,1-benzoxazine in Example 13.

The title compound was prepared according to the procedure for Example 13 from 2-methyl-6-bromospiro[4H-3,1-benzoxazine-4,1'-cyclopentane] and 5-bromo-4-methyl-2-thiophenecarbonitrile. A yellowish solid: mp 58–60° C.; $^1$H-NMR (DMSO-d$_6$) δ 7.79 (s, 1H), 7.16 (d, 1H, J=1.9 Hz), 7.12 (dd, 1H, J=8.4, 2.2 Hz), 6.66 (s, 1H), 6.63 (d, 1H, J 8.4 Hz), 4.75 (m, 1H), 2.26 (s, 3H), 2.14 (m, 1H), 1.87 (m, 1H), 1.4–1.7 (m, 6H), 1.32 (d, 3H, J=5.5 Hz).

EXAMPLE 24

4-(2-Methylspiro[2H-3,1-benzoxazine-4,1'-cyclopentane]-6-yl)-2-thiophenecarbonitrile Prepared according to the procedure for Example 13 from 2-methyl-6-bromospiro[4H-3,1-benzoxazine-4,1'-cyclopentane] and 4-bromo-2-thiophenecarbonitrile. An off-white solid: mp 103–104° C.

EXAMPLE 25

5-(2-methylspiro[2H-3,1-benzoxazine-4,1'-cyclohexane]-6yl)-4-methyl-2-thiophenecarbonitrile 2-Methyl-6-bromospiro[2H-3,1-benzoxazine-4,1'-cyclohexane] was prepared using the same procedure as for 6-bromo-2,4,4-trimethyl-1,4-dihydro-2H-3,1-benzoxazine in Example 13.

The title compound was prepared according to the procedure for Example 13 from 2-methyl-6-bromospiro[4H-3,1-benzoxazine-4,1'-cyclohexane] and 5-bromo-4-ethyl-2-thiophenecarbonitrile. A brown solid: $^1$H-NMR (DMSO-d$_6$) δ 7.78 (s, 1H), 7.17 (d, 1H, J=1.8 Hz), 7.14 (dd, 1H, J=8.4, 2.2 Hz), 6.64 (s, 1H), 6.63 (d, 1H, J=82 Hz), 4.74 (m, 1H), 2.26 (s, 3H), 2.14 (m, 1H), 1.87 (m, 1H), 1.4–1.7 (m, 8H), 1.31 d, 3H, J=5.3 Hz); MS (ESI) m/z 337 [M−−H]$^-$.

EXAMPLE 26

4-(2-Methylspiro[2H-3,1-benzoxazine-4,1'-cyclohexane]-6-yl)2-thiophenecarbonitrile Prepared according to the procedure for Example 13 from 2-methyl-6-bromospiro[4H-3,1-benzoxazine-4,1'-cyclohexane] and 4-bromo-2-thiophenecarbonitrile. A brown solid: mp 111–112° C.; $^1$H-NMR (DMSO-d$_6$) δ 8.42 (s, 1H), 8.14 (s, 1H), 7.47 (s, 1H), 7.35 (dd, 1H, J=8.3, 1.1 Hz), 6.58 (d, 1H, J=8.4 Hz), 6.38 (s, 1H), 4.72 (m, 1H), 1.92–2.16 (m, 2H), 1.35–1.75 (m, 8H), 1.31 (d, 3H, J=5.3 Hz); MS (ESI) m/z 325 [M+H]$^+$.

EXAMPLE 27

6-(3-Fluorophenyl)-2,4,4-trimethyl-1,4-dihydro-2H-3,1-benzoxazine

Prepared according to the coupling procedure for Example 17 from 3-fluorophenyl boronic acid and 6-bromo-2,4,4-trimethyl-1,4-dihydro-2H-3,1-benzoxazine. A yellow solid: mp 139–140° C.; $^1$H-NMR (CDCl$_3$) δ 7.40–7.19 (m, 6H), 7.01–6.94 (m, 1H), 6.72 (d, 1H, J=8.24 Hz), 4.90 (q, 1H, J=5.48 Hz), 1.62 (s, 3H), 1.59 (s, 3H), 1.46 (d, 3H, J=5.5 Hz); MS (ES) m/z 272 ([M+H]$^+$).

EXAMPLE 28

6-(3-Chlorophenyl)-2,4,4-trimethyl-1,4-dihydro-2H-3,1-benzoxazine

Prepared according to the coupling procedure for Example 17 from 3-chlorophenyl boronic acid and 6-bromo-2,4,4-trimethyl-1,4-dihydro-2H-3,1-benzoxazine. A orange solid: mp 144–146° C.; $^1$H-NMR (CDCl$_3$) δ 7.50 (t, 1H, J=1.78 Hz), 7.40 (dt, 1H, J=7.61, 1.45 Hz), 7.33 (t, 1H, J=7.76 Hz), 7.29–7.22 (m, 4H) 6.72 (d, 1H, J=8.24 Hz), 4.90 (q, 1H, J=5.45 Hz), 1.62 (s, 3H), 1.59 (s, 3H), 1.46 (d, 3H, J=5.5 Hz); MS (ES) m/z 288/290 ([M+H]$^+$).

EXAMPLE 29

6(3-Chloro-4-fluorophenyl)-2,4,4-trimethyl-1,4dihydro-2H-3,1-benzoxazine

A mixture of 6-bromo-2,4,4-trimethyl-1,4-dihydro-2H-3,1-benzoxazine (3.0 g, 11.7 mmol), 3-chloro-4-fluorobenzeneboronic acid (3.1 g, 17.6 mmol), tetrakis(triphenylphosphine)palladium (0) (0.67 g, 0.59 mmol), and sodium carbonate (3.72 g, 35.1 mmol) in DME (80 mL) and water (40 mL) was subject to a blanket of nitrogen flow for 15 minutes at 50° C. and then was heated at 85° C. under nitrogen for 1 hour. The reaction was cooled to room temperature and ethyl acetate (200 mL) was added. The organic layer was washed twice with aqueous ammonium chloride (50 mL) and once with brine (50 mL), dried over sodium sulfate and concentrated to a yellow solid. The solid was triturated with ether (25 mL) and hexane (25 mL), collected on a filter, and dried to give 6-(3-chloro-4-fluorophenyl)-2,4,4-trimethyl-1,4-dihydro-2H-3,1-benzoxazine (1.87 g, 35%) as a yellow solid: mp 173–175° C.; $^1$H-NMR (DMSO-d$_6$) δ 7.79 (dd, 1H, J=6.84, 2.14 Hz), 7.60–7.57 (m, 1H), 7.43–7.39 (m, 2H), 7.29 (dd, 1H, J=8.12, 2.14 Hz), 6.62 (d, 1H, J=8.54 Hz), 6.40 (s, 1H), 4.79 (q, 1H, J=5.55 Hz), 1.53 (s, 3H), 1.48 (s, 3H), 1.28 (d, 3H, J=5.55 Hz); MS (ES) m/z 306/308([M +H]$^+$).

EXAMPLE 30

2-Fluoro-5-(2,4,4-trimethyl-1,4-dihydro-2H-3,1-benzoxazin-6-yl)benzonitrile

Prepared according to the coupling procedure for Example 13 from 6-bromo-2,4,4-trimethyl-1,4-dihydro-2H-3,1-benzoxazine and 5-bromo-2-fluorobenzonitrile. A white solid: mp 184–186° C.; $^1$H-NMR (DMSO-d$_6$) δ 8.17 (dd, 1H, J=5.86, 3.42 Hz), 8.00–7.98 (m, 1H), 7.52 (t, 1H, J=9.28 Hz), 7.45 (d, 1H, J=1.95 Hz), 7.34 (dd, 1H, J=8.30, 1.95 Hz), 6.63 (d, 1H, J=8.3 Hz), 6.45 (d, 1H), 4.8 (q, 1H, J=5.37 Hz), 1.53 (s, 3H), 1.49 (s, 3H), 1.29 (d, 3H, J=5.37 Hz); MS (ES) m/z 297 ([M+H]$^+$).

EXAMPLE 31

4-(2,4,4-Trimethyl-1,4-dihydro-2H-3,1-benzoxazin-6-yl)-2-furonitrile

Prepared using the coupling procedure for Example 13 from 6-bromo-2,4,4-trimethyl-1,4-dihydro-2H-3,1-benzoxazine and 4-bromo-2-cyanofuran. A light brown solid: mp 116–118° C.; $^1$H-NMR (DMSO-d$_6$) δ 8.43 (s, 1H), 8.06 (s, 1H), 7.38 (d, 1H, J=1.98 Hz), 7.25 (dd, 1H, J=7.93, 1.98 Hz) 6.58 (d, 1H, J=7.93 Hz), 6.37 (s, 1H), 4.77 (q, 1H, J=5.55 Hz), 1.50 (s, 3H), 1.46 (s, 3H), 1.27 (d, 3H, J=5.55 Hz); MS (ES) m/z 269 ([M+H]$^+$); Anal. Calc. For C$_{16}$H$_{16}$N$_2$O$_2$: C, 71.62; H, 6.01, N, 10.44. Found: C, 71.55; H, 6.26, N, 10.17.

EXAMPLE 32

3-[4,4-Dimethyl-2-(trifluoromethyl)-1,4-dihydro-2H-3,1-benzoxazin-6-yl]-5-fluorobenzonitrile A mixture of 2-(2-amino-5-bromo-phenyl)-propan-2-ol (5 g, 21.7 mmol), trifluoroacetaldehyde methyl hemiacetal (5 mL), and magnesium sulfate (10 g) in toluene (75 mL) was heated at 80° C. under nitrogen. After disappearance of the starting material, the reaction was filtered through a pad of silica gel and the filtrate dried over sodium sulfate and concentrated to give 6-bromo-4,4-dimethyl-2-(trifluoromethyl)-1,4-dihydro-2H-3,1-benzoxazine as an amorphous solid: $^1$H-NMR (DMSO-d$_6$) δ 7.31 (d, 1H, J=1.99 Hz), 7.19 (dd, 1H, J=8.73, 2.38 Hz), 6.88 (s 1H), 6.74 (d, 1H, J=8.33 Hz), 5.32 (m, 1H), 1.52 (s, 6H).

A mixture of 6-bromo-4,4-dimethyl-2-(trifluoromethyl)-I,4-dihydro-2H-3,1-benzoxazine (0.5 g, 1.61 mmol), 3-cyano-5-fluorobenzeneboronic acid (0.39 g, 1.8 mmol), tetrakis(triphenylphosphine)-palladium (0) (0.2 g, 0.161 mmol), and sodium carbonate (0.5 g, 4.83 mmol) in DME (50 mL) and water (25 mL) was subject to a blanket of nitrogen flow for 15 minutes at 50° C. and then was heated at 85° C. under nitrogen for 1 hour. The reaction mixture was cooled to room temperature and ethyl acetate (200 mL) was added. The organic layer was washed twice with aqueous ammonium chloride (20 mL) and once with brine (20 mL), dried over sodium sulfate and concentrated to a yellow solid. Purification via flash column chromatography (silica gel, 5% ethyl acetate/hexane) gave 3-[4,4-dimethyl-2-(trifluoromethyl)-1,4-dihydro-2H-3,1-benzoxazin-6-yl]-5-fluorobenzonitrile (0.396 g, 73%) as a white solid: mp 102–103° C.; $^1$H-NMR (DMSO-d$_6$) δ 8.07 (s, 1H), 7.91 (d, 1H, J=10.7 Hz), 7.7 (d, 1H, J=10.7 Hz) 7.62 (d, 1H, J=1.98 Hz), 7.53 (dd, 1H, J=8.33, 1.98 Hz), 7.05 (s, 1H), 6.87 (d, 1H, J=8.33 Hz), 5.39–5.37 (m, 1H), 1.61 (s, 3H), 1.59 (s, 3H); MS (ES) m/z 349 ([M–H]$^-$).

EXAMPLE 33

4-[4,4-Dimethyl-2-(trifluoromethyl)-1,4-dihydro-2H-3,1-benzoxazin-6-yl]thiophene2carbonitrile Prepared using the coupling procedure for Example 13 starting with 6-bromo-4,4-dimethyl-2-(trifluoromethyl)-1,4-dihydro-2H-3,1-benzoxazine and 4-bromo-2-thiophenecarbonitrile. A yellow solid: $^1$H-NMR (DMSO-d$_6$) δ 8.43 (s, 1H), 8.19 (s, 1H), 7.54 (d, 1H, J=1.98 Hz), 7.46 (dd,1H, J=8.33, 1.98 Hz), 6.90 (s, 1H), 6.83 (d, 1H, J=8.33 Hz), 5.35 (d, 1H, J=3.57 Hz), 1.59 (s, 3H), 1.57 (s, 3H); MS (ES) m/z 337 ([M–H]$^-$).

EXAMPLE 34

4-[1-Acetyl-4,4-dimethyl-2-(trifluoromethyl)-1,4-dihydro-2H-3,1-benzoxazin-6-yl]thiophene-2-carbonitrile 4-[4,4-dimethyl-2-(trifluoromethyl)-1,4-dihydro-2H-3,1-benzoxazin-6-yl]thiophene-2-carbonitrile (0.25 g, 0.74 mmol) was dissolved in DMF (10 mL), NaH (0.09 g, 2.22 mmol) was added and the mixture was stirred for 30 minutes prior to the addition of acetyl chloride (0.079 mL, 1.11 mmol). Upon disappearance of the starting material the reaction mixture was poured into brine (100 mL) and the product extracted with ether (150 mL), dried over sodium sulfate and concentrated. The residue was purified by a flash column chromatography (silica gel, 25% ethyl acetate/hexane) to yield 4-[1-acetyl-4,4-dimethyl-2-(trifluoromethyl)-1,4-dihydro-2H-3,1-benzoxazin-6-yl]thiophene-2-carbonitrile (0.1 g, 36%) as an amorphous solid: $^1$H-NMR (DMSO-d$_6$) δ 8.58 (s, 1H), 8.5 (s, 1H), 7.83–7.80 (m, 2H), 7.64 (d, 1H, J=8.74 Hz), 6.42 (q, 1H, J=10 Hz), 2.24 (s, 3H), 1.73 (s, 3H), 1.42 (s, 3H).

EXAMPLE 35 (6(5-Cyanothien-3-yl)-4,4-dimethyl-2 (tnfluoromethyl)-2H-3,1-benzoxazin-1(4H)-yl)methyl Pivalate 4-[4,4-dimethyl-2-(trifluoromethyl)-1,4-dihydro-2H-3,1-benzoxazin-6-yl]thiophene-2-carbonitrile (0.30 g, 0.89 mmol) was dissolved in DMF (10 mL), NaH (0.065 g, 2.7 mmol) was added and the was mixture stirred for 30 minutes prior to the addition of tert-butyl chloroacetate (0.19 mL, 1.3 mmol). Upon disappearance of the starting material the reaction mixture was poured into brine (100 mL) and the product extracted with ether (150 mL), dried over sodium sulfate and concentrated. Flash column chromatography (silica gel, 8% ethyl acetate/hexane) gave (6(5-cyanothien-3-yl)-4,4-dimethyl-2-(trifluoromethyl)-2H-3,1-benzoxazin-1 (4H)-yl)methyl pivalate (0.127 g, 32%) as an amorphous solid: $^1$H-NMR (CDCl$_3$) δ 7.82 (s, 1H), 7.58 (s, 1H), 7.41 (dd, 1H, J=8.33, 1.98 Hz), 7.25 (d, 1H, J=1.98 Hz) 7.10 (d, 1H, J=8.33 Hz), 6.79 (d, 1H, J=8.33 Hz), 5.66 (d, 1H, J=11.9 Hz), 5.38 (d, 1H, J=11.9 Hz), 1.72 (s, 3H), 1.55 (s, 3H), 1.18 (s, 9H).

EXAMPLE 36

3-Fluoro-5-(2,2,4,4-tetramethyl-1,4dihydro-2H-3,1-benzoxazin-6-yl)benzonitrile

Prepared using the coupling procedure for Example 13 starting with 6-bromo-2,2,4,4-tetramethyl-1,4-dihydro-2H-3,1-benzoxazine and 3-bromo-5-fluorobenzonitrile. A white solid: $^1$H-NMR (DMSO-d$_6$) δ 8.03 (s, 1H), 7.87 (d, 1H, J=10.7 Hz), 7.65 (d, 1H, J=10.7 Hz), 7.57 (d, 1H, J=1.98 Hz) 7.45 (dd, 1H, J=8.33, 1.98 Hz), 6.65 (d, 1H, J=8.33 Hz), 6.42 (s, 1H), 1.52 (s, 6H), 1.34 (s, 6H); MS (ES) m/z 311 ([M+H]$^+$).

EXAMPLE 37

4(2,2,4,4-Tetramethyl-1,4-dihydro-2H-3,1-benzoxazin-6-yl)thiolphene-2-carbonitrile Prepared using the coupling procedure for Example 13 starting with 6-bromo-2,2,4,4-tetramethyl-1,4-dihydro-2H-3,1-benzoxazine and 4-bromo-2-cyanothiophene. An amorphous orange solid: $^1$H-NMR (DMSO-d$_6$) δ 8.4 (d, 1H, J=1.69 Hz), 8.14 (d, 1H, J=1.69 Hz), 7.49 (d, 1H, J=2.20 Hz), 7.38 (dd, 1H, J=8.43, 2.02 Hz), 6.61 (d, 1H, J=8.43 Hz), 6.26 (s, 1H), 1.49 (s, 6H), 1.32 (s, 6H); MS (ES) m/z 299 ([M+H]$^+$).

EXAMPLE 38

5-[4,4-Dimethyl-2-(trifluoromethyl)-1,4-dihydro-2H-3,1-benzoxazin-6yl]-4-methylthiophene-2-carbonitrile Prepared according to the coupling procedure for Example 13 from 6-bromo-4,4-dimethyl-2-(trifluoromethyl)-1,4-dihydro-2H-3,1-benzoxazine and 5-bromo-4-methyl-2-thiophene-carbonitrile. A yellowish solid: mp 97–98° C.; $^1$H-NMR (DMSO-d$_6$) δ 7.82 (s, 1H), 7.26 (d, 1H, J=1.7 Hz), 7.21 (dd, 1H, J=8.1, 2.1 Hz), 7.16 (s, 1H), 6.88 (d, 1H, J=8.1 Hz), 5.40 (m, 1H), 2.27 (s, 3H), 1.56 (s, 3H), 1.55 (s, 3H); MS (ESI) m/z 351 [M–H]$^-$.

EXAMPLE 39

6-(3-Chlorophenyl)-4,4-dimethyl-2-(trifluoromethyl)-1,4-dihydro-2H-3,1-benzoxazine Prepared according to the coupling procedure for Example 17 from 6-bromo-4,4-dimethyl-2-(trifluoromethyl)-1,4-dihydro-2H-3,1-benzoxazine and 3-chlorophenyl boronic acid. A yellowish solid: mp 108–109° C.; $^1$H-NMR (DMSO-d$_6$) δ 7.69 (t, 1H, J=1.7 Hz), 7.59 (d, 1H, J=7.8 Hz), 7.35–7.50 (m, 3H), 7.32 (dt, 1H, J=8.1, 1.1 Hz), 6.91 (s, 1H), 6.87 (d, 1H, J=8.4 Hz), 5.35 (m, 1H), 1.60 (s, 3H), 1.59 (s, 3H); MS (ESI) m/z 340 [M–H]$^-$.

EXAMPLE 40

6(3-Fluorophenyl)-4,4-dimethyl-3,4-dihydroquinolin-2(1H)-one

Prepared by coupling 3-fluorophenylboronic acid with an equivalent amount of 6-bromo-4,4-dimethyl-3,4-dihydro-1H-quinolin-2-one using a catalytic amount of tetrakis (triphenylphosphine)palladium(0) with overnight refluxing in toluene containing an equivalent amount of potassium carbonate dissolved in water. Work up in the usual manner followed by recrystallization from ethanol gave a grey solid: mp 190–192° C. $^1$H-NMR (DMSO-d$_6$) δ 10.27 (s, 1H), 7.57 (s, 1H), 7.50 (m, 4H), 7.15 (m, 1H), 6.95 (d, 1H J=8.2 Hz), 2.39 (s, 2H), 1.29 (s, 6H); MS (APCI (–)) m/z 268 [M–H]$^-$ Anal. Calc. For C$_{17}$H$_{16}$FNO 0.25 H$_2$O: C, 74.57, H, 6.07, N, 5.12. Found: C, 74.86, H, 5.97, N 5.06.

EXAMPLE 41

3-(4,4-Dimethyl-2-oxo-1,2,3,4-tetrahydroquinolin-6-yl)-5-fluorobenzonitrile 6-bromo-4,4-quinolin-2-one was allowed to couple with an equivalent of bis(pinacolato)diboron in refluxing DMF containing an equivalent of sodium carbonate dissolved in a minimal amount of water and a catalytic quantity of tetrakis (triphenylphosphine)palladium(0). After refluxing overnight an equivalent of 3-bromo-5-fluorobenzonitrile was added. Another equivalent of sodium carbonate was then added, followed by an additional amount of the same catalyst. After several hours of reflux, the reaction mixture was filtered and taken to dryness in vacuo. The residue was extracted into ethyl acetate and the solution was dried over magnesium sulfate, filtered and the filtrate was again roto-evaporated to give a solid residue. Recrystallization from ethanol afforded the title compound as a grey solid: mp 249–250° C. $^1$H-NMR (DMSO-d$_6$) δ 10.32 (s, 1H), 8.09 (t, 1H, J=1.6 Hz), 7.93 (d, 1H, J=12.7 Hz) 7.77, (d, 1H, J=8.1 Hz), 7.70 (s, 1H), 7.61(d, 1H J=8.9 Hz), 6.95 (d, 1H, J=8.3 Hz),2.40 (s, 2H), 1.30 (s, 6H); MS (APCI (–)) m/z 293 [M–H]$^-$ Anal. Calc. For C$_{18}$H$_{15}$FN$_2$O 1.5H$_2$O: C, 67.28, H, 5.65, N, 8.72. Found: C, 67.36, H, 4.90, N s8.44.

EXAMPLE 42

3-(4,4-Dimethyl-2-oxo-1,2,3,4-tetrahydroquinolin-6-yl)benzonitrile

Prepared by coupling 3-cyanophenylboronic acid with an equivalent amount of 6-bromo-4,4-dimethyl-3,4-dihydro- 1H-quinolin-2-one using a catalytic amount of tetrakis(triphenylphosphine)palladium(0) as a catalyst with overnight refluxing in toluene containing an equivalent amount of potassium carbonate dissolved in water in the usual manner followed by recrystallization from ethanol gave a grey solid: mp. 190–192° C.; $^1$H-NMR (DMSO-d$_6$) δ 10.29 (s,1H), 8.17 (s, 1H), 8.00 (d,1H, J=7.9 Hz), 7.77 (d, 1H, J=6.4 Hz), 7.65 (m, 2H), 7.55 (d, 1H, J=8.2 Hz), 6.97 (d, 1H, J=8.3 Hz), 2.40 (s, 2H), 1.30 (s, 6H); MS (APCI (–)) m/z 275 [M–-H]$^-$ Anal. Calc. For C$_{18}$H$_{16}$N$_2$O 0.25H$_2$O: C, 75.77, H, 6.01, N, 9.82. Found: C, 75.45, H, 5.65, N 9.20.

EXAMPLE 43

6-(3-Chlorophenyl)-4,4-dimethyl-3,4-dihydroquinoline-2(1H)-thione

Prepared by heating under reflux overnight a mixture of 6-(3-chlorophenyl)-4,4-dimethyl-3,4-dihydroquinoline-2 (1H)-one and an equal weight of phosphorus pentasulfide in pyridine was stirred. Removal of the pyridine in vacuo followed by treating the residue with 6N hydrochloric acid and recrystallization of the residue in ethanol gave the product as a yellow solid: mp. 197–1980° C. $^1$H-NMR (DMSO-d$_6$) δ 12.34 (s, 1H), 7.75 (m, 1H), 7.64 (m, 2H), 7.57 (dd, 1H J=9.3 and 2.1 Hz), 7.48 (t, 1H, J=7.7 Hz), 7.41 (m, 1H), 7.20 (d, 1H, J=8.3 Hz), 3.34 (s, 2H), 1.26 (s,6H); MS (APCI (–)) m/z 300 [M–H]$^-$ Anal. Calc. For C$_{17}$H$_{16}$ClNS: C, 67.65, H, 5.34, N, 4.64. Found: C, 67.77, H, 5.57, N 4.54.

EXAMPLE 44

6-(3-Fluorophenyl)-4,4-dimethyl-3,4-dihydroquinoline-2(1H)-thione

Prepared by heating under reflux overnight a mixture of 6-(3-fluororophenyl)-4,4-dimethyl-3,4-dihydroquinoline-2 (1H)-one and an equal weight of phosphorus pentasulfide was stirred in pyridine. Workup as in the previous example gave a yellow solid, mp 209–211° C. $^1$H-NMR (DMSO-d$_6$) δ 12.34 (s,1H), 7.65 (d,1H J=2.2 Hz) 7.57 (dd , 1H J$_1$=8.24 J$_2$=2.2 Hz), 7.51 (m, 3H), 7.18(m, 2H), 2.84(s, 2H), 1.26(s, 5H). MS m/z 284 [M–H]$^-$ Anal. Calc. For C$_{17}$H$_{16}$FlNS: C,71.55, H,5.65, N,4.91. Found: C,71.18, H,5.59, N4.82.

EXAMPLE 45

3-(4,4-Dimethyl-2-thioxo-1,2,3,4,-tetrahydroquinolin-6-yl)benzonitrile

Prepared by heating under reflux overnight a stirred mixture of 3-(4,4-dimethyl-2-oxo-1,2,3,4,-tetrahydroquinolin-6-yl)benzonitrile and an equal weight of phosphorus pentasulfide in pyridine and workup as in the previous example gave a yellow solid: mp 220–223° C. dec. $^1$H-NMR (DMSO-d$_6$) δ 12.35 (s, 1H), 8.21 (s, 1H), 8.10 (d, 1H, J=6.0 Hz), 7.80 (d, 1H, J=7.9 Hz), 7.72 (s, 1H), 7.65 (m, 2H), 7.21 (d, 1H, J=8.4 Hz), 2.85 (s, 2H), 1.27 (s, 6H); MS (APCI (–)) m/z 291 [M–H]$^-$ Anal. Calc. For C$_{18}$H$_{16}$N$_2$S 3H$_2$O: C, 62.40, H, 6.40, N, 8.09. Found: C, 62.12, H, 4.88, N 7.77.

EXAMPLE 46

3-(4,4-Dimethyl-2-thioxo-1,2,3,4-tetrahydroquinolin-6-yl)5-fluorobenzonitrile

Prepared by heating under reflux overnight a stirred mixture of 3-(4,4-dimethyl-2-oxo-1,2,3,4-tetrahydroquinolin-6-yl)-5-fluorobenzonitrile and an equal weight of phosphorus pentasulfide in pyridine and workup as in the previous example gave a yellow solid: mp. 240–242° C. dec.; $^1$H-NMR (DMSO-d$_6$) δ 12.37 (s, 1H), 8.13 (s, 1H), 7.98 (dt,1H, J=10.4 and 5.4 Hz), 7.81 (d, 1H, J=8.4 Hz), 7.7 (d, 1H, J=1.8 Hz), 7.68 (dd, 1H, J=8.3 and 1.9 Hz), 7.22 (d, 1H, J=8.3 Hz), 2.85 (s, 2H), 1.27 (s, 6H); MS m/z 309 [M–H]$^-$ Anal. Calc. For C$_{18}$H$_{15}$FN$_2$S 0.10 H$_2$O: C, 69.25, H, 4.91, N, 8.97. Found: C, 69.15, H, 4.74, N 8.75.

EXAMPLE 47

6(3-Fluoro-phenyl)-2,4,4trimethyl-12,3,4tetrahydroquinoline

6-Bromo-1-(4-methoxy-benzyl)-4,4-dimethyl-3,4-dihydro-1H-quinolin-2-one.

To a solution of 6-bromo-4,4-dimethyl-3,4-dihydro-1H-quinolin-2-one (0.5 g, 1.97 mmol) in THF (25 mL) was added 60% NaH (0.12 g, 2.95 mmol) suspended in mineral oil. The resulting reaction mixture was stirred at room temperature for 30 min., 4-methoxybenzyl chloride (0.34 g, 2.17) added, and heated under reflux for 20 h. The reaction was cooled to room temperature then quenched slowly with water. After extraction with ethyl acetate, the organic layer was dried (MgSO$_4$), evaporated and the residue purified by chromatography (SiO$_2$ 3:7 ethyl acetate/hexane). The white crystalline product was obtained (0.35 g, 48%); mp 118–119° C., $^1$H NMR (DMSO-d$_6$) δ 1.23 (s, 6H), 2.59 (s, 2H), 3.70 (s, 3H), 3.72 (s, 1H), 4.41 (d, 1H, J=5.86 Hz), 5.09 (s, 1H), 6.87 (m, 2H), 7.01 (d, 1H, J=8.78 Hz), 7.17 (d, 1H, J=8.98 Hz), 7.23 (d, 1H, J=8.79), 7.34 (dd, 1H, J=6.59 and 2.2 Hz), 7.43(d, 1H, J=2.2 Hz); MS (APCI (+)) [M+H]$^+$= 374/376.

6-(3-Fluoro-phenyl)-1-(4-methoxy-benzyl)-4,4-dimethyl-3, 4-dihydro-1H-quinolin-2-one.

A mixture of 6-Bromo-1-(4-methoxy-benzyl)-4,4-dimethyl-3,4-dihydro-1H-quinolin-2-one (2.9 g, 7.75 mmol) in ethylene glycol dimethyl ether (50 mL), K$_2$CO$_3$ (1.18 g, 8.53 mmol) in H$_2$O (5.0 mL), and a catalytic amount of tetrakistriphenylphosphine palladium was heated under reflux overnight. After cooling to room temperature, the mixture was extracted with ethyl acetate and the organic phase was washed with NaHCO$_3$ solution, brine, dried over MgSO$_4$, concentrated, and crystallized from ethanol to obtain the product as a white crystalline material (1.8 g, 60%): mp 159–162° C., $^1$H NMR (DMSO-d$_6$) δ 1.32 (s, 6H), 2.63 (s, 2H ), 3.70 (s, 3H), 5.15 (s, 2H), 6.89 (d, 2H, J=11.72 Hz), 7.14 (m, 2H), 7.22 (d, 2H, J=8.8 Hz), 7.53 (m, 4H), 7.60 (d, 1H, J=2.2 Hz), MS (APCI (+)) [M+H]$^+$=390.

6-Bromo-1-(4-methoxy-benzyl)-2,4,4-trimethyl-1,4-dihydro-quinoline.

To a solution of 6-(3-Fluoro-phenyl)-1-(4-methoxy-benzyl)-4,4-dimethyl-3,4-dihydro-1H-quinolin-2-one (1.16 g, 2.99 mmol) in THF (15 mL) at room temperature was added a solution of 1.4 M MeMgBr (2.6 mL, 12.56 mmol) and the resulting reaction mixture was stirred for 6 h. The solution was quenched with H$_2$O, extracted with EtOAc, treated with ammonium chloride solution, washed with brine, dried over MgSO$_4$, and concentrated. The product was purified by column chromatography using a 2:8 hexane/ethyl acetate mixture and used below.

To a solution of 6-(3-Fluoro-phenyl)-1-(4-methoxy-benzyl)-2,4,4-trimethyl-1,2,3,4-tetrahydroquinoline (0.15 g, 0.39 mmol) in EtOH (35 mL) was added 10% Pd/C and hydrogenated for 10 h at 40 psi. The catalyst was removed by filtration through celite and the product purified by chromatography. A reddish liquid was obtained. $^1$H NMR (DMSO-d$_6$) δ 1.15 ( d, 3H, J=6.73 Hz), 1.21(s, 3H), 1.34(m, 4H), 1.60( dd, 1H, $J_1 = 10.1$, $J_2 = 2.69$, Hz), 3.40( m, 1H), 5.95 (s, 1H), 6.55( d, 1H, J=8.08 Hz), 7.01 (m, 1H), 7.21(dd, 1H, $J_1$=5.78 $J_2$=2.02 Hz), 7.35 (m, 4H); MS(Fl Pos) $[M+H]^+$= 270.

Still other compounds, including 5-(2,4,4-Trimethyl-1,2, 3,4-tetrahydro-quinolin-6-yl)-1H-pyrrole-2-carbonitrile, 1-Methyl-5-(2,4,4-trimethyl-1,2,3,4-tetrahydro-quinolin-6-yl)-1H-pyrrole-2- carbonitrile, and 3-Fluoro-5-(2,4,4-trimethyl-1,2,3,4-tetrahydro-quinolin-6-yl)-benzonitrile may be prepared using the methods described above.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:

1. A method of contraception, which comprises administering to a female of child bearing age for 28 consecutive days:
   a) a first phase of from 14 to 24 daily dosage units of a progestational agent equal in progestational activity to about 35 to about 100 µg levonorgestrel;
   b) a second phase of from 1 to 11 daily dosage units, at a daily dosage of from about 2 to 50 mg, of an antiprogestin compound of Formula I:

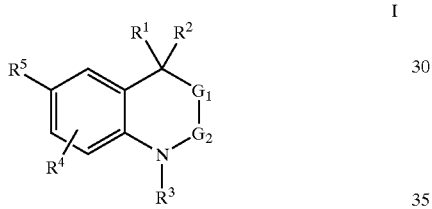

I wherein:
$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$;
or $R^1$ and $R^2$ are fused to form:
   (i) a carbon-based saturated 3 to 8 membered spirocyclic ring,
   (ii) a carbon-based 3 to 8 membered spirocyclic ring having one or more carbon—carbon double bonds; or
   (iii) a 3 to 8 membered spirocyclic, heterocyclic ring having in its backbone one to three heteroatoms selected from the group consisting of O, S and N;
   the spirocyclic rings of (i), (ii), and (iii) being optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, NH2, NH($C_1$ to $C_6$ alkyl), and N($C_1$ to $C_6$ alkyl)$_2$;
$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl,
$R^B$ is H, $C_1$ to $C_3$ alkyl, or substituted $C_1$ to $C_3$ alkyl;
$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, or $COR^C$;

$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl,
$R^4$ is H, halogen, CN, $NO_2$, $C_1$ to $C_6$ alkyl, substituted $C_1$ to $C_6$ alkyl, alkynyl, substituted alkynyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;
$R^5$ is (iv) or (v):
   (iv) a substituted benzene ring of the structure:

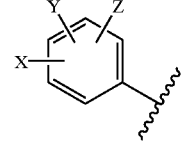

X is selected from the group consisting of halogen, CN, $C_1$ to $C_3$ alkyl, substituted $C_1$ to $C_3$ alkyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^D$, $OCOR^D$, and $NR^ECOR^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
Y and Z are independent substituents selected from the group consisting of H, halogen, CN, $NO_2$, amino, aminoalkyl, $C_1$ to $C_3$ alkoxy, $C_1$ to $C_3$ alkyl, and $C_1$ to $C_3$ thioalkoxy; or
   (v) a five or six membered ring having in its backbone 1, 2, or 3 heteroatoms selected from the group consisting of O, S, SO, $SO_2$ and $NR^6$ and having one or two independent substituents selected from the group consisting of H, halogen, CN, $NO_2$, amino, $C_1$ to $C_3$ alkyl, $C_1$ to $C_3$ alkoxy, $C_1$ to $C_3$ aminoalkyl, $COR^F$, and $NR^GCOR^F$;
$R^F$ is H, $C_1$ to $C_3$ alkyl, substituted $C_1$ to $C_3$ alkyl, aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^G$ is H, $C_1$ to $C_3$ alkyl, or substituted $C_1$ to $C_3$ alkyl;
$R^6$ is H or $C_1$ to $C_3$ alkyl;
$G_1$ is $NR_7$ or $CR_7R_8$;
$G_2$ is CO or $CR_7R_8$; provided that $G_1$ and $G_2$ cannot both be $CR_7R_8$;
$R_7$ and $R_8$ are independently selected from the group consisting of H, alkyl, substituted alkyl, aryl, and heterocyclic;
or pharmaceutically acceptable salt thereof; and
c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

2. The method according to claim 1 wherein the progestational agent is levonorgestrel and wherein:

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^4$ is H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, amino, $C_1$ to $C_6$ aminoalkyl, or substituted $C_1$ to $C_6$ aminoalkyl;

$R^5$ is (vi) or (vii):

(vi) the substituted benzene ring of the structure:

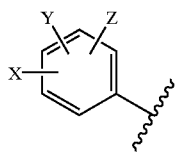

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 membered heterocyclic ring having in its backbone 1 to 3 heteroatoms, $COR^D$, $OCOR^D$, and $NR^ECOR^D$;

Y and Z are independent substituents selected from the group consisting of H, halogen, CN, $NO_2$, $C_1$ to $C_3$ alkoxy, $C_1$ to $C_3$ alkyl, and $C_1$ to $C_3$ thioalkoxy; or (vii) the five or six membered ring having in its backbone 1, 2, or 3 heteroatoms selected from the group consisting of O, S, SO, $SO_2$ and $NR^6$ and having one or two independent substituents selected from the group consisting of H, halogen, CN, $NO_2$, amino, $C_1$ to $C_3$ alkyl, and $C_1$ to $C_3$ alkoxy.

3. The method according to claim 1 wherein the progestational agent is levonorgestrel and the anti-progestin compound has the structure:

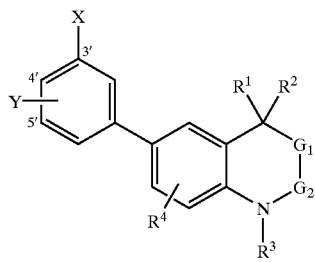

wherein:
$R^1=R^2$ and are selected from the group consisting of $C_1$ to $C_3$ alkyl and substituted $C_1$ to $C_3$ alkyl, or $R^1$ and $R^2$ are fused to form the carbon-based saturated 3 to 6 membered spirocyclic ring (i);

$R^3$ is H, OH, $NH_2$, $C_1$ to $C_6$ alkyl, substituted $C_1$ to $C_6$ alkyl, or $COR^C$;

$R^C$ is H, $C_1$ to $C_3$ alkyl, or $C_1$ to $C_3$ alkoxy;

$R^4$ is H, halogen, $NO_2$, $C_1$ to $C_3$ alkyl, or substituted $C_1$ to $C_3$ alkyl;

X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring having in its backbone 1 to 3 heteroatoms, and $C_1$ to $C_3$ thioalkoxy, Y is on the 4' or 5' position and is selected from the group consisting of H, halogen, CN, $NO_2$, $C_1$ to $C_3$ alkoxy, $C_1$ to $C_3$ alkyl, and $C_1$ to $C_3$ thioalkoxy.

4. The method according to claim 1 wherein the progestational agent is levonorgestrel and the anti-progestin compound has the structure:

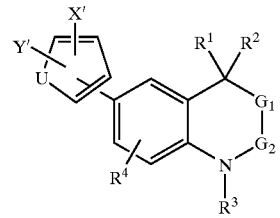

wherein:
$R^1=R^2$ and are selected from the group consisting of $C_1$ to $C_3$ alkyl and substituted $C_1$ to $C_3$ alkyl, or $R^1$ and $R^2$ are fused to form the carbon-based saturated 3 to 6 membered spirocyclic ring (i);

$R^3$ is H, OH, $NH_2$, $C_1$ to $C_6$ alkyl, substituted $C_1$ to $C_6$ alkyl, or $COR^C$;

$R^C$ is H, $C_1$ to $C_3$ alkyl, or $C_1$ to $C_3$ alkoxy, $R^4$ is H, halogen, $NO_2$, $C_1$ to $C_3$ alkyl, or substituted $C_1$ to $C_3$ alkyl;

U is O, S, or $NR^6$,

X' is selected from the group consisting of .halogen, CN, $NO_2$, $C_1$ to $C_3$ alkyl, and $C_1$ to $C_3$ alkoxy, Y' is selected from the group consisting of H and $C_1$ to $C_3$ alkyl.

5. The method according to claim 1 wherein the progestational agent is levonorgestrel and the anti-progestin compound has the structure:

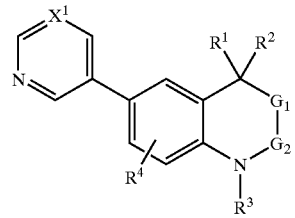

wherein:
$R^1=R^2$ and are selected from the group consisting of $C_1$ to $C_3$ alkyl and substituted $C_1$ to $C_3$ alkyl, or $R^1$ and $R^2$ are fused to form the carbon-based saturated 3 to 6 membered spirocyclic ring (i), $R^3$ is H, OH, $NH_2$, $C_1$ to $C_6$ alkyl, substituted $C_1$ to $C_6$ alkyl, or $COR^C$;

$R^C$ is H, $C_1$ to $C_3$ alkyl, or $C_1$ to $C_3$ alkoxy;

$R^4$ is H, halogen, $NO_2$, $C_1$ to $C_3$ alkyl, or substituted $C_1$ to $C_3$ alkyl;

$X^1$ is N or $CX^2$;

$X^2$ is halogen, CN, $C_1$ to $C_3$ alkoxy, or $NO_2$.

6. The method according to claim 1 in which the anti-progestin compound is 6-(3-Chlorophenyl)-4-cyclopropyl-1H-quinazolin-2-one or a pharmaceutically acceptable salt thereof.

7. The method according to claim 1 in which the antiprogestin compound is 6-(3-Chlorophenyl)-4-cyclopropyl-1-(4-methoxybenzyl)-1H-quinazolin-2-one or a pharmaceutically acceptable salt thereof.

8. The method according to claim 1 in which the antiprogestin compound is 6-(3-Chlorophenyl)-4-cyclopropyl-4-methyl-3,4-dihydro-1H-quinazolin-2-one or a pharmaceutically acceptable salt thereof.

9. The method according to claim 1 in which the antiprogestin compound is 6-(3-Chlorophenyl)-4-cyclopropyl-3,4-dimethyl-3,4-dihydro-1H-quinazolin-2-one or a pharmaceutically acceptable salt thereof.

10. The method according to claim 1 in which the antiprogestin compound is 6-(3-Chloro-phenyl)-4,4-dimethyl-3,4-dihydro-1H-quinolin-2-one or a pharmaceutically acceptable salt thereof.

11. The method according to claim 1 wherein the progestational agent is selected from the group consisting of levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, and (17-deacetyl) norgestimate.

12. The method according to claim 1 which comprises administering to a female of child bearing age consecutively over a 28 day cycle:
 a) a first phase of 21 daily dosage units of a progestational agent equal in progestational activity to about 35 to about 100 μg levonorgestrel;
 b) a second phase of 3 daily dosage units of an antiprogestin compound of formula 1, each daily dosage unit containing an antiprogestin compound at a daily dosage of from about 2 to 50 mg; and
 c) optionally, 4 daily dosage units of an orally and pharmaceutically acceptable placebo to be administered on each day of the 28-day cycle following the first phase and second phase.

13. The method according to claim 1 in which the antiprogestin compound is 6-(3-Fluorophenyl)-4,4-dimethyl-3,4-dihydroquinolin-2(1H)-one or a pharmaceutically acceptable salt thereof.

14. The method according to claim 1 in which the antiprogestin compound is 3-(4,4-Dimethyl-2-oxo-1,2,3,4-tetrahydroquinolin-6-yl)-5-fluorobenzonitrile or a pharmaceutically acceptable salt thereof.

15. The method according to claim 1 in which the antiprogestin compound is 3-(4,4-Dimethyl-2-oxo-1,2,3,4-tetrahyoroquinolin-6-yl)-benzonitrile or a pharmaceutically acceptable salt thereof.

16. A method of contraception which comprises administering to a female of child bearing age for 28 consecutive days:
 a) a first phase of from 14 to 24 daily dosage units of a progestational agent equal in progestational activity to about 35 to about 100 μg levonorgestrel;
 b) a second phase of from 1 to 11 daily dosage units, at a daily dosage of from about 2 to 50 mg, of an antiprogestin compound of Formula I:

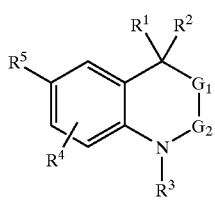

I wherein:
 $R^1$ and $R^2$ are the same and are selected from the group consisting of $C_1$ to $C_3$ alkyl and substituted $C_1$ to $C_3$ alkyl, or $R^1$ and $R^2$ are fused to form a carbon-based saturated 3 to 6 membered spirocyclic ring;
 $R^3$ is H, OH, $NH_2$, $C_1$ to $C_6$ alkyl, substituted $C_1$ to $C_6$ alkyl, or $COR^C$;
 $R^C$ is H, $C_1$ to $C_4$ alkyl, or $C_1$ to $C_4$ alkoxy;
 $R^4$ is H, halogen, $NO_2$, $C_1$ to $C_3$ alkyl, or substituted $C_1$ to $C_3$ alkyl;
 $R^5$ is selected from the group consisting of (i), (ii), and (iii):
 (i) a substituted benzene ring of the formula:

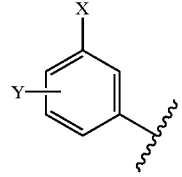

wherein:
 X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring having in its backbone 1 to 3 heteroatoms, and $C_1$ to $C_3$ thioalkoxy,
 Y is on the 4' or 5' position and is selected from the group consisting of H, halogen, CN, $NO_2$, $C_1$ to $C_3$ alkoxy, $C_1$ to $C_4$ alkyl, and $C_1$ to $C_3$ thioalkoxy;
 (ii) a five-membered ring of the structure:

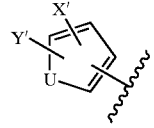

wherein:
 U is O, S, or $NR^6$;
 X' is selected from the group consisting of halogen, CN, $NO_2$, $C_1$ to $C_3$ alkyl, and $C_1$ to $C_3$ alkoxy;
 Y' is selected from the group consisting of H and $C_1$ to $C_4$ alkyl;
 $R^6$ is selected from the group consisting of H, $C_1$ to $C_3$ alkyl, and $C_1$ to $C_4$ $CO_2$alkyl; and
 (iii) a six-membered ring of the formula:

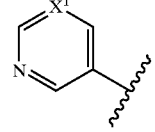

wherein:
 $X^1$ is N or $CX^2$;
 $X^2$ is halogen, CN, $C_1$ to $C_3$ alkoxy, or $NO_2$; and
 $G_1$ is $NR_7$ or $CR_7R_8$;
 $G_2$ is CO or $CR_7R_8$; provided that $G_1$ and $G_2$ cannot both be $CR_7R_8$;
 $R_7$ and R are independently selected from the group consisting of H, alkyl, substituted alkyl, substituted aryl, and substituted heterocyclic;
 c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

17. A method of contraception which comprises administering to a female of child bearing age for 28 consecutive days:

a) a first phase of from 14 to 24 daily dosage units of a progestational agent equal in progestational activity to about 35 to about 100 μg levonorgestrel;
b) a second phase of from 1 to 11 daily dosage units, at a daily dosage of from about 2 to 50 mg, of an antiprogestin compound of Formula I:

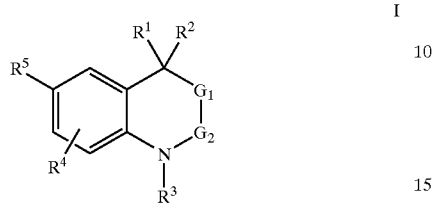

wherein:
$R^1$ and $R^2$ are the same and are $C_1$ alkyl or $R^1$ and $R^2$ are fused to form a carbon-based saturated 3 to 6 membered spirocyclic ring;
$R^3$ is H, OH, $NH_2$, $C_1$ alkyl, substituted $C_1$ alkyl, or $COR^C$;
$R^C$ is H, $C_1$ to $C_3$ alkyl, or $C_1$ to $C_4$ alkoxy;
$R^4$ is H, halogen, $NO_2$, or $C_1$ to $C_3$ alkyl;
$R^5$ is selected from the group consisting of (i) and (ii):
(i) a substituted benzene ring of the formula:

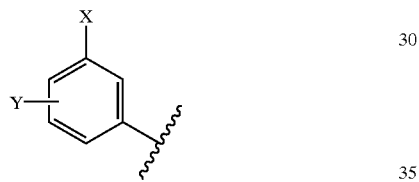

wherein:
X is selected from the group consisting of halogen, CN, $C_1$ alkoxy, $NO_2$, and 2-thiazole;
Y is on the 4' or 5' position and is selected from the group consisting of H and F; and
(ii) a five-membered ring of the structure:

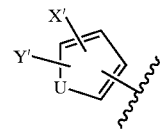

wherein:
U is O, S, or NH;
X' is selected from the group consisting of halogen, CN, and $NO_2$;
Y' is selected from the group consisting of H and $C_1$ to $C_4$ alkyl;
$G_1$ is $NR_7$ or $CR_7R_8$;
$G_2$ is CO or $CR_7R_8$; provided that $G_1$ and $G_2$ cannot both be $CR_7R_8$;
$R_7$ and $R_8$ are independently selected from the group consisting of H, alkyl, substituted alkyl, substituted aryl, and substituted heterocyclic;

c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

* * * * *

UNITED STATES PATENT AND TRADEMARK OFFICE
CERTIFICATE OF CORRECTION

PATENT NO.    : 6,498,154 B1
DATED         : December 24, 2002
INVENTOR(S)   : Grubb et al.

It is certified that error appears in the above-identified patent and that said Letters Patent is hereby corrected as shown below:

Column 3,
Line 46, replace "higand" with -- ligand --.
Line 68, replace "95" with -- 1995 --.

Column 6,
Line 22, replace "norgestiimate" with -- norgestimate --.

Column 7,
Line 3, insert after "each" the word -- of --.

Column 13,
Line 66, insert after "thereof", -- . --.

Column 14,
Delete lines 34-45.

Column 15,
Line 12, after "atom" insert -- . --.

Column 16,
Line 16, change "an" to -- a --.

Column 19,
Line 64, change "-I" to -- 1 --.

Column 23,
Line 60, change "similar" to -- similar --.

Column 25,
Line 48, change "intrapentoneally" to -- intraperitoneally --.

Column 26,
Lines 5 and 42, change "1-(4Amino" to -- 1-(4-Amino --.

Column 27,
Line 27, change "acetatelhexane" to -- acetate/hexane --.
Line 47, change "$0_30$" to -- $0_3.0$ --.
Line 51, change "4Amino" to -- 4-Amino --.

UNITED STATES PATENT AND TRADEMARK OFFICE
CERTIFICATE OF CORRECTION

PATENT NO. : 6,498,154 B1  
DATED : December 24, 2002  
INVENTOR(S) : Grubb et al.

Page 2 of 4

It is certified that error appears in the above-identified patent and that said Letters Patent is hereby corrected as shown below:

Column 28,  
Line 9, change "6(3" to -- 6-(3 --.  
Line 31, change "ayellowish" to -- a yellowish --.  
Line 41, change "6-(3Chloro" to -- 6-(3-Chloro --.

Column 29,  
Lines 46-47, change "dimethyl13, 4dihydro" to -- dimethyl-3,4-dihydro --.

Column 30,  
Line 11, change "$Cl_2$" to -- $ClN_2$ --.

Column 32,  
Line 19, change "plasrmid" to -- plasmid --.  
Line 26, change "mediutm" to -- medium --.  
Line 27, insert a -- . -- after "medium".  
Line 32, change "Pronmega" to -- Promega --.

Column 33,  
Line 5, change "EC50" to -- IC50 --.  
Line 13, change "Progestatinal" to -- Progestational --.  
Line 19, change "maxi" to -- maximal --.  
Line 32, change "10 U/ml" to -- 100 U/ml --.  
Lines 33 and 39, change "streptornycin" to -- streptomycin --.

Column 34,  
Line 36, change "cinfident" to -- confident --.  
Line 58, change "streptomycin" to -- streptomycin --.

Column 35,  
Line 28, change "fill" to -- full --.  
Line 13, change "ovariectony" to -- ovariectomy --.

Column 37,  
Line 16, change "0.03, 0.29, 0.60" to -- 0.05, 0.22, 0.67 --.  
Line 38, change "(mg/kg,s.c.)" to -- (mg/k.g,p.o.) -- .  
Line 56, change "$EC_5o$" to -- $EC_{50}$ --.

Column 38,  
Line 56, change "3-Bomo" to -- 3-bromo --.

UNITED STATES PATENT AND TRADEMARK OFFICE
CERTIFICATE OF CORRECTION

PATENT NO.   : 6,498,154 B1
DATED        : December 24, 2002
INVENTOR(S)  : Grubb et al.

It is certified that error appears in the above-identified patent and that said Letters Patent is hereby corrected as shown below:

Column 39,
Line 10, change "4-Methyl-5(2" to -- 4-Methyl-5(2 --.

Column 40,
Line 13, change "carboxlate" to -- carboxylate --.

Column 41,
Line 3, change "6-yl)1H" to -- 6-yl)-1H --.
Line 7, change "nimol" to -- mmol --.
Line 31, change "5cyano" to -- (5-cyano --.
Line 42, change "(3x5 mL)" to -- (3x15ml) --.
Line 55, change "1-Methyl-S" to -- 1-Methyl-5 --.

Column 42,
Line 2, change "5(2" to -- 5-(2 --.
Line 39, change "4-ethyl" to -- 4-methyl --.
Line 42, change "J=82 Hz" to -- J=8.2 Hz --.

Column 43,
Line 20, change "6(3" to -- 6-(3 --.
Line 21, change "4dihydro" to -- 4-dihydro --.

Column 44,
Line 47, change "thiophene2carbontrile" to -- thiophene-2-carbonitrile --.

Column 45,
Line 12, "EXAMPLE 35" should be centered two lines down form the line above.
Lines 12-13, change "4-dimethyl-2(tnfluoromethyl)" to -- 4-dimethyl-2-(trifluoromethyl) --.
Line 17, change "the was mixture" to -- the mixture was --.
Line 34, change "1,4dihydro" to -- 1,4-dihydro --.
Line 47, change "4(2" to -- 4-(2 --.
Line 61, change "6y1" to -- 6-yl --.

Column 46,
Line 21, change "6(3" to -- 6-(3 --.

Column 47,
Line 23, change "1980 to -- 198 --.
Line 42, change "5H)." to -- 6H --.
Line 64, change "6-yl)5" to -- 6-yl)-5 --.

UNITED STATES PATENT AND TRADEMARK OFFICE
CERTIFICATE OF CORRECTION

PATENT NO.    : 6,498,154 B1
DATED         : December 24, 2002
INVENTOR(S)   : Grubb et al.

It is certified that error appears in the above-identified patent and that said Letters Patent is hereby corrected as shown below:

Column 48,
Line 12, change "6(3-Fluoro-phenyl2,4,4trimethyl" to -- 6-(3-Fluoro-phenyl)-2,4,4-trimethyl --.

Signed and Sealed this

Twentieth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,498,154 B1
DATED : December 24, 2002
INVENTOR(S) : Grubb et al.

It is certified that error appears in the above-identified patent and that said Letters Patent is hereby corrected as shown below:

Column 3,
Line 46, replace "higand" with -- ligand --.
Line 68, replace "95" with -- 1995 --.

Column 6,
Line 22, replace "norgestiimate" with -- norgestimate --.

Column 7,
Line 3, insert after "each" the word -- of --.

Column 13,
Line 66, insert after "thereof", -- . --.

Column 14,
Delete lines 34-45.

Column 15,
Line 12, after "atom" insert -- . --.

Column 16,
Line 16, change "an" to -- a --.

Column 19,
Line 64, change "-I" to -- 1 --.

Column 23,
Line 60, change "similar" to -- similar --.

Column 25,
Line 48, change "intrapentoneally" to -- intraperitoneally --.

Column 26,
Line 5, change "1-(4Amino" to -- 1-(4-Amino --.
Line 42, change "1-(4Amino" to -- 1-(4-Amino --.

UNITED STATES PATENT AND TRADEMARK OFFICE
CERTIFICATE OF CORRECTION

PATENT NO.    : 6,498,154 B1
DATED         : December 24, 2002
INVENTOR(S)   : Grubb et al.

It is certified that error appears in the above-identified patent and that said Letters Patent is hereby corrected as shown below:

Column 27,
Line 27, change "acetatelhexane" to -- acetate/hexane --.
Line 47, change "$0_30$" to -- $0_30$ --.
Line 51, change "4Amino" to -- 4-Amino --.

Column 28,
Line 9, change "6(3" to -- 6-(3 --.
Line 31, change "ayellowish" to -- a yellowish --.
Line 41, change "6-(3Chloro" to -- 6-(3-Chloro --.

Column 29,
Lines 46-47, change "dimethyl13, 4dihydro" to -- dimethyl-3,4-dihydro --.

Column 30,
Line 11, change "$Cl_2$" to -- $ClN_2$ --.

Column 32,
Line 19, change "plasrmid" to -- plasmid --.
Line 26, change "mediutm" to -- medium --.
Line 27, insert a -- . -- after "medium".
Line 32, change "Pronmega" to -- Promega --.

Column 33,
Line 5, change "EC50" to -- IC50 --.
Line 13, change "Progestatinal" to -- Progestational --.
Line 19, change "maxi" to -- maximal --.
Line 32, change "10 U/ml" to -- 100 U/ml --.
Lines 33 and 39, change "streptornycin" to -- streptomycin --.

Column 34,
Line 36, change "cinfident" to -- confident --.
Line 58, change "streptomycin" to -- streptomycin --.

Column 35,
Line 28, change "fill" to -- full --.
Line 13, change "ovariectony" to -- ovariectomy --.

UNITED STATES PATENT AND TRADEMARK OFFICE
CERTIFICATE OF CORRECTION

PATENT NO.    : 6,498,154 B1
DATED         : December 24, 2002
INVENTOR(S)   : Grubb et al.

It is certified that error appears in the above-identified patent and that said Letters Patent is hereby corrected as shown below:

Column 37,
Line 16, change "0.03, 0.29, 0.60" to -- 0.05, 0.22, 0.67 --.
Line 38, change "(mg/kg,s.c.)" to -- (mg/k.g,p.o.) --.
Line 56, change "EC$_5$o" to -- EC$_{50}$ --.

Column 38,
Line 56, change "3-Bomo" to -- 3-bromo --.

Column 39,
Line 10, change "4-Methyl-5(2" to -- 4-Methyl-5(2 --.

Column 40,
Line 13, change "carboxlate" to -- carboxylate --.

Column 41,
Line 3, change "6-yl)1H" to -- 6-yl)-1H --.
Line 7, change "nimol" to -- mmol --.
Line 31, change "5cyano" to -- (5-cyano --.
Line 42, change "(3x5 mL)" to -- 3x15ml) --.
Line 55, change "1-Methyl-S" to -- 1-Methyl-5 --.

Column 42,
Line 2, change "5(2" to -- 5-(2 --.
Line 39, change "4-ethyl" to -- 4-methyl --.
Line 42, change "J=82 Hz" to -- J=8.2 Hz --.

Column 43,
Line 20, change "6(3" to -- 6-(3 --.
Line 21, change "4dihydro" to -- 4-dihydro --.

Column 44,
Line 47, change "thiophene2carbontrile" to -- triophene-2-carbonitrile --.

Column 45,
Line 12, "EXAMPLE 35" should be centered two lines down from the line above.
Lines 12-13, change "4-dimethyl-2(tnfluoromethyl)" to -- 4-dimethyl-2-(trifluoromethyl) --.
Line 17, change "the was mixture" to -- the mixture was --
Line 34, change "1,4dihydro" to -- 1,4-dihydro --.
Line 47, change "4(2" to -- 4-(2 --.

UNITED STATES PATENT AND TRADEMARK OFFICE
CERTIFICATE OF CORRECTION

PATENT NO. : 6,498,154 B1
DATED : December 24, 2002
INVENTOR(S) : Grubb et al.

It is certified that error appears in the above-identified patent and that said Letters Patent is hereby corrected as shown below:

Column 45 (con't,)
Line 61, change "6yl" to -- 6-yl --.

Column 46,
Line 21, change "6(3" to -- 6-(3 --.

Column 47,
Line 23, change "1980" to -- 198 --.
Line 42, change "5H)." to -- 6H --.
Line 64, change "6-yl)5" to -- 6-yl)-5 --.

Column 48,
Line 12, change "6(3-Fluoro-pheny12,4,4trimethyl" to -- 6-(3-Fluoro-phenyl)-2,4,4-trimethyl --.

Signed and Sealed this

Seventeenth Day of February, 2004

JON W. DUDAS
*Acting Director of the United States Patent and Trademark Office*